United States Patent
Rahfeld et al.

(10) Patent No.: US 12,043,659 B2
(45) Date of Patent: Jul. 23, 2024

(54) HUMANIZED AND DE-IMMUNIZED ANTIBODIES

(71) Applicant: VIVORYON THERAPEUTICS N.V., Halle (DE)

(72) Inventors: Jens-Ulrich Rahfeld, Gemeinde Seegebiet Mansfelder Land (DE); Stephen Gillies, Carlisle, MA (US); Thore Hettmann, Teltow (DE); Stephan Schilling, Halle (DE); Martin Kleinschmidt, Halle (DE)

(73) Assignee: VIVORYON THERAPEUTICS N.V., Halle (DE)

( * ) Notice: Subject to any disclaimer, the term of this patent is extended or adjusted under 35 U.S.C. 154(b) by 959 days.

(21) Appl. No.: 16/964,892

(22) PCT Filed: Jan. 29, 2019

(86) PCT No.: PCT/EP2019/052100
§ 371 (c)(1),
(2) Date: Jul. 24, 2020

(87) PCT Pub. No.: WO2019/149689
PCT Pub. Date: Aug. 8, 2019

(65) Prior Publication Data
US 2021/0032315 A1    Feb. 4, 2021

(30) Foreign Application Priority Data
Jan. 31, 2018  (EP) .................... 18154427

(51) Int. Cl.
C07K 16/00    (2006.01)
A61K 47/06    (2006.01)

(52) U.S. Cl.
CPC .............. *C07K 16/00* (2013.01); *A61K 47/06* (2013.01); *C07K 2317/565* (2013.01)

(58) Field of Classification Search
CPC .............. C07K 16/00; C07K 2317/565; C07K 2317/24; C07K 2317/71; C07K 2317/92; C07K 2317/94; C07K 16/18; A61K 47/06; A61K 2039/505; A61P 25/28
See application file for complete search history.

(56) References Cited

FOREIGN PATENT DOCUMENTS
WO    WO2017009459 A2    1/2017

OTHER PUBLICATIONS

Sean H Gao et al: "Monoclonal antibody humanness score and its applications", BMC Biotechnology, Biomed Central Ltd. London, GB, vol. 13, No. 1, Jul. 5, 2013 (Jul. 5, 2013), pp. 55, XP021156542, ISSN: 1472-6750, DOI: 10.1186/1472-6750-13-55.

Yaghoub Safdari et al: "Antibody humanization methods—a review and update", Biotechnology and Genetic Engineering Reviews, vol. 29, No. 2, Oct. 1, 2013 (Oct. 1, 2013), GB, pp. 175-186, XP055250530, ISSN: 0264-8725, DOI: 10.1080/02648725.2013.801235.

Anonymous: "Antibody Humanization | Antibody Engineering", Mar. 9, 2016 (Mar. 9, 2016), XP055256758, Retrieved from the Internet <URL:https://lakepharma.com/productlist.php?category=2&secondary=3> [retrieved on Mar. 9, 2016].

Anonymous: "Antitope—Antibody humanization", Mar. 9, 2016 (Mar. 9, 2016), XP055256546, Retrieved from the Internet <URL:http://www.antitope.com/antibody-humanization> [retrieved on Mar. 9, 2016].

*Primary Examiner* — Jessica H Roark
*Assistant Examiner* — Francesca Edgingtongiordan
(74) *Attorney, Agent, or Firm* — Olson & Cepuritis, Ltd.

(57) ABSTRACT

The invention relates to humanized and de-immunized antibodies that bind to an epitope at the N-terminus of pyroglutamated amyloid beta (Aβ N3pE) peptide and to preventive and therapeutic treatment of diseases and conditions that are related to accumulation and deposition of amyloid peptides, such as amyloidosis, a group of disorders and abnormalities associated with pyroglutamated amyloid peptide, like Alzheimer's disease, Down's syndrome, cerebral amyloid angiopathy and other related aspects. More specifically, it pertains to the use of monoclonal antibodies of the invention to bind pyroglutamated amyloid beta peptide in plasma, brain, and cerebrospinal fluid to prevent accumulation or to reverse deposition of Aβ N3pE within the brain and in various tissues in the periphery, and to alleviate amyloidosis. The present invention further pertains to diagnostic assays for the diagnosis of amyloidosis using the antibodies of the invention.

14 Claims, 4 Drawing Sheets
Specification includes a Sequence Listing.

A

B

A

B

HUMANIZED AND DE-IMMUNIZED ANTIBODIES

CROSS-REFERENCE TO RELATED APPLICATIONS

This application is a U.S. National Stage of PCT/EP2019/052100, filed Jan. 29, 2019, which claims priority to European Application No. 18154427.1, filed Jan. 31, 2018, each of which is incorporated herein by reference.

FIELD OF THE INVENTION

The invention relates to humanized and de-immunized antibodies that bind to an epitope at the N-terminus of pyroglutamated amyloid beta (Aβ N3pE) peptide and to preventive and therapeutic treatment of diseases and conditions that are related to accumulation and deposition of amyloid peptides, such as amyloidosis, a group of disorders and abnormalities associated with pyroglutamated amyloid peptide, like Alzheimer's disease, Down's syndrome, cerebral amyloid angiopathy and other related aspects. More specifically, it pertains to the use of monoclonal antibodies of the invention to bind pyroglutamated amyloid beta peptide in plasma, brain, and cerebrospinal fluid to prevent accumulation or to reverse deposition of Aβ N3pE within the brain and in various tissues in the periphery, and to alleviate amyloidosis. The present invention further pertains to diagnostic assays for the diagnosis of amyloidosis using the antibodies of the invention.

BACKGROUND ART

Amyloidosis is not a single disease entity but rather a diverse group of progressive disease processes characterized by extracellular tissue deposits of a waxy, starch-like protein called amyloid, which accumulates in one or more organs or body systems. As the amyloid deposits accumulate, they begin to interfere with the normal function of the organ or body system. There are at least 15 different types of amyloidosis. The major forms are primary amyloidosis without known antecedent, secondary amyloidosis following some other condition, and hereditary amyloidosis.

Secondary amyloidosis occurs during chronic infection or inflammatory disease, such as tuberculosis, a bacterial infection called familial Mediterranean fever, bone infections (osteomyelitis), rheumatoid arthritis, inflammation of the small intestine (granulomatous ileitis), Hodgkin's disease and leprosy. Amyloid deposits include amyloid P (pentagonal) component (AP), a glycoprotein related to normal serum amyloid P (SAP), and sulphated glycosaminoglycans (GAG), complex carbohydrates of connective tissue. Amyloid protein fibrils, which account for about 90% of the amyloid material, comprise one of several different types of proteins. These proteins are capable of folding into so-called "beta-pleated" sheet fibrils, a unique protein configuration which exhibits binding sites for Congo red resulting in the unique staining properties of the amyloid protein.

Many diseases of aging are based on or associated with amyloid-like proteins and are characterized, in part, by the buildup of extracellular deposits of amyloid or amyloid-like material that contribute to the pathogenesis, as well as the progression of the disease. These diseases include, but are not limited to, neurological disorders such as mild cognitive impairment (MCI), Alzheimer's disease (AD), like for instance sporadic Alzheimer's disease (SAD) or Familial Alzheimer's dementias (FAD) like Familial British Dementia (FBD) and Familial Danish Dementia (FDD), neurodegeneration in Down Syndrome, Lewy body dementia, hereditary cerebral hemorrhage with amyloidosis (Dutch type); the Guam Parkinson-Dementia complex. Other diseases which are based on or associated with amyloid-like proteins are progressive supranuclear palsy, multiple sclerosis; Creutzfeld Jacob disease, Parkinson's disease, HIV-related dementia, ALS (amyotropic lateral sclerosis), Adult Onset Diabetes; senile cardiac amyloidosis; endocrine tumors, and others, including macular degeneration.

Although pathogenesis of these diseases may be diverse, their characteristic deposits often contain many shared molecular constituents. To a significant degree, this may be attributable to the local activation of pro-inflammatory pathways thereby leading to the concurrent deposition of activated complement components, acute phase reactants, immune modulators, and other inflammatory mediators (McGeer et al., Tohoku J Exp Med. 174(3): 269-277 (1994)).

Recently, accumulating evidence demonstrates involvement of N-terminal modified Aβ peptide variants in Alzheimer's disease. Aiming biopsies display a presence of Aβ 1-40 and Aβ 1-42 not only in the brain of Alzheimer's patients but also in senile plaques of unaffected individuals. However, N-terminal truncated and pyroGlu modified Aβ N3pE-40/Aβ N3pE-42 is almost exclusively engrained within plaques of Alzheimer's disease patients, making this Aβ variant an eligible diagnostic marker and a potential target for drug development.

At present, several commercial manufacturers offer ELISA kits which allow a detection of Aβ 1-40/1-42 and Aβ N3pE-40/Aβ N3pE-42 in the low picogram (pg) range.

The brains of Alzheimer's disease (AD) patients are morphologically characterized by the presence of neurofibrillary tangles and by deposits of Aβ peptides in neocortical brain structures (Selkoe, D. J. & Schenk, D. Alzheimer's disease: molecular understanding predicts amyloid-based therapeutics. Annu. Rev. Pharmacol. Toxicol. 43, 545-584 (2003)). Aβ peptides are liberated from the amyloid precursor protein (APP) after sequential cleavage by β- and γ-secretase. The γ-secretase cleavage results in the generation of Aβ 1-40 and Aβ 1-42 peptides, which differ in their C-termini and exhibit different potencies of aggregation, fibril formation and neurotoxicity (Shin, R. W. et al. Amyloid beta-protein (Abeta) 1-40 but not Abeta 1-42 contributes to the experimental formation of Alzheimer disease amyloid fibrils in rat brain. J. Neurosci. 17, 8187-8193 (1997); Iwatsubo, T. et al. Visualization of Abeta 42(43) and Abeta 40 in senile plaques with end-specific Abeta monoclonals: evidence that an initially deposited species is Abeta 42(43). Neuron 13, 45-53 (1994); Iwatsubo, T., Mann, D. M., Odaka, A., Suzuki, N. & Ihara, Y. Amyloid beta protein (Abeta) deposition: Abeta 42(43) precedes Abeta 40 in Down syndrome. Ann. Neurol. 37, 294-299 (1995); Hardy, J. A. & Higgins, G. A. Alzheimer's disease: the amyloid cascade hypothesis. Science 256, 184-185 (1992); RoBner, S., Ueberham, U., Schliebs, R., Perez-Polo, J. R. & Bigl, V. The regulation of amyloid precursor protein metabolism by cholinergic mechanisms and neurotrophin receptor signaling. Prog. Neurobiol. 56, 541-569 (1998)).

The majority of Aβ peptides deposited in diffuse plaques are N-terminal truncated or modified. Studies of Piccini and Saido have shown that the core structure of senile plaques and vascular deposits consist of 50% pyroglutamate (pyroGlu) modified peptides (Piccini et al., J Biol Chem. 2005 Oct. 7; 280(40):34186-92; Saido et al., Neuron. 1995 February; 14(2): 457-66). PyroGlu modified peptides are more strongly cytotoxic than other Aβ species and stable against aminopeptidases (Russo et al., J Neurochem. 2002 September; 82(6):1480-9). Thus, pyroGlu Aβ species have a longer half-life whereby the accumulation of these species and the formation of neurotoxic oligomers as well as aggregates are beneficial (Saido, Neurobiol Aging. 1998 January-February; 19(1 Suppl):S69-75). Due to the cyclization of glutamate to pyroGlu, charged amino acids will be lost which strongly reduces the solubility of the peptide and causes an increased aggregation tendency. In vitro studies have shown that the initial oligomerisation of e.g. Aβ3 (pE) is much faster compared to non-modified peptides (Schilling et al., Biochemistry. 2006 Oct. 17; 45(41):12393-9). The Aβ N3pE-42 peptides coexist with Aβ 1-40/1-42 peptides (Saido, T. C. et al. Dominant and differential deposition of distinct beta-amyloid peptide species, Abeta N3pE, in senile plaques. Neuron 14, 457-466 (1995); Saido, T. C., Yamao, H., Iwatsubo, T. & Kawashima, S. Amino- and carboxyl-terminal heterogeneity of beta-amyloid peptides deposited in human brain. *Neurosci. Lett.* 215, 173-176 (1996)), and, based on a number of observations, could play a prominent role in the pathogenesis of Aβ. For example, a particular neurotoxicity of Aβ N3pE-42 peptides has been outlined (Russo, C. et al. Pyroglutamate-modified amyloid beta-peptides—AbetaN3(pE)—strongly affect cultured neuron and astrocyte survival. *J. Neurochem.* 82, 1480-1489 (2002) and the pE-modification of N-truncated Aβ peptides confers resistance to degradation by most aminopeptidases as well as Aβ-degrading endopeptidases (Russo, C. et al. Pyroglutamate-modified amyloid beta-peptides—AbetaN3(pE)—strongly affect cultured neuron and astrocyte survival. *J. Neurochem.* 82, 1480-1489 (2002); Saido, T. C. Alzheimer's disease as proteolytic disorders: anabolism and catabolism of beta-amyloid. *Neurobiol. Aging* 19, S69-S75 (1998)). The cyclization of glutamic acid into pE leads to a loss of N-terminal charge resulting in accelerated aggregation of Aβ N3pE compared to the unmodified Aβ peptides (He, W. & Barrow, C. J. The Abeta 3-pyroglutamyl and 11-pyroglutamyl peptides found in senile plaque have greater beta-sheet forming and aggregation propensities in vitro than full-length A beta. *Biochemistry* 38, 10871-10877 (1999); Schilling, S. et al. On the seeding and oligomerization of pGlu-amyloid peptides (in vitro). *Biochemistry* 45, 12393-12399 (2006)). Thus, reduction of Aβ N3pE-42 formation should destabilize the peptides by making them more accessible to degradation and would, in turn, prevent the formation of higher molecular weight Aβ aggregates and enhance neuronal survival.

However, for a long time it was not known how the pE-modification of Aβ peptides occurs. Recently, it was discovered that glutaminyl cyclase (QC) is capable to catalyze Aβ N3pE-42 formation under mildly acidic conditions and that specific QC inhibitors prevent Aβ N3pE-42 generation in vitro (Schilling, S., Hoffmann, T., Manhart, S., Hoffmann, M. & Demuth, H.-U. Glutaminyl cyclases unfold glutamyl cyclase activity under mild acid conditions. *FEBS Lett.* 563, 191-196 (2004); Cynis, H. et al. Inhibition of glutaminyl cyclase alters pyroglutamate formation in mammalian cells. *Biochim. Biophys. Acta* 1764, 1618-1625 (2006)).

All facts suggest that pyroGlu Aβ is a kind of germ for the initialization of fibril formation. In a further study (Piccini et al., 2005, supra) volunteers with plaque depositions but without AD specific pathology could be distinguished from AD patients due to the characteristic amount of Aβ-species. Thereby the amount of N-terminal truncated, pyroGlu modified peptides was significant higher in the brain of AD patients.

The posttranslational formation of pyroGlu at position 3 or 11 of Aβ-peptide implies cyclization of an N-terminal glutamate residue. Glutaminyl cyclase (QC) plays an important role in the generation of pyroGlu peptides. QC is wide-spread in the plant- and animal kingdom and inter alia, is involved in the maturation of peptide hormones. Both the cyclisation of glutamine by release of ammonia and of glutamate by release of water to pyroGlu is performed by QC. In contrast to the glutamine cyclization the glutamate cyclisation occurs not spontaneously. QC catalyses the efficient (unwanted) side reaction from glutamate to pyroGlu. The generated pyroGlu residue protects the protein against proteolytic degradation. There are several references which shows that QC plays an important role in the generation of pyroGlu Aβ:

1. In several studies it was shown that QC catalyses the formation of pyroGlu residues from glutamate at N-terminus of Aβ (Cynis et al., Biochim Biophys Acta. 2006 October; 1764(10):1618-25, Schilling et al., FEBS Lett. 2004 Apr. 9; 563(1-3):191-6);
2. Both Aβ peptides and QC are expressed in large quantities in hippocampus and cortex. These brain areas are at particular risk in AD (Pohl et al., Proc Natl Acad Sci USA. 1991 Nov. 15; 88(22):10059-63, Selkoe, Physiol Rev. 2001 April; 81(2):741-66);
3. The APP is cleaved by β-secretase during the transport to the plasma membrane whereby the N-terminus of Aβ with the free glutamate residue can be produced (Greenfield et al., Proc Natl Acad Sci USA. 1999 Jan. 19; 96(2):742-7). In the secretory vesicles a co-localisation of processed APP and the QC was determined. So in the mild acid milieu of the vesicles an accelerated modification of glutamate residue to pyroglutamate can occur.
4. Also other neurodegenerative diseases (familiar Danish (FDD) or British dementia (FBD)) are related with N-terminal pyroGlu modified peptides e.g. Bri2, but in contrast they are not related to A β in terms of their primary structure (Vidal R. et al., 1999 Proc. Natl. Acad. Sci. U.S.A. 97, 4920-4925).

Possibly the QC-catalysed formation of pyroGlu Aβ is involved in the development and progression of neurodegenerative diseases. The formation of N-terminal modified amyloid peptides certainly represents a fundamental factor in the process of Aβ aggregation and could be the onset of disease. The suppression of the pyroGlu Aβ formation by inhibition of QC, might represent a therapeutic approach. QC inhibitors would be able to prevent the formation of pyroGlu Aβ, reduce the concentration of pyroglutamate Aβ in the brain and so delay the oligomerisation of Aβ-peptides. Schilling et al. show, that QC expression was up regulated in the cortex of AD patients and correlated with the appearance of pyroGlu-modified Aβ-peptide. Oral application of a QC inhibitor resulted in reduced pyroglutamate modified AβpE(3-42) level in two different transgenic mouse models of AD and in a new *Drosophila* model (Schilling et al., 2008 *Biol. Chem.* (389), 983-991).

Lewy body dementia (LBD) is a neurodegenerative disorder that can occur in persons older than 65 years of age, and typically causes symptoms of cognitive (thinking) impairment and abnormal behavioral changes. Symptoms can include cognitive impairment, neurological signs, sleep disorder, and autonomic failure. Cognitive impairment is the presenting feature of LBD in most cases. Patients have recurrent episodes of confusion that progressively worsen. The fluctuation in cognitive ability is often associated with shifting degrees of attention and alertness. Cognitive impairment and fluctuations of thinking may vary over minutes, hours, or days. Lewy bodies are formed from phosphorylated and nonphosphorylated neurofilament proteins; they contain the synaptic protein alpha-synuclein as well as ubiquitin, which is involved in the elimination of damaged or abnormal proteins. In addition to Lewy Bodies, Lewy neurites, which are inclusion bodies in the cell processes of the nerve cells, may also be present. Amyloid plaques may form in the brains of patients afflicted with DLB, however they tend to be fewer in number than seen in patients with Alzheimer's disease. Neurofibrillary tangles, the other micropathological hallmark of AD, are not a main characteristic of LBD but are frequently present in addition to amyloid plaques.

Amyotrophic lateral sclerosis (ALS) is characterized by degeneration of upper and lower motor neurons. In some ALS patients, dementia or aphasia may be present (ALS-D). The dementia is most commonly a frontotemporal dementia (FTD), and many of these cases have ubiquitin-positive, tau-negative inclusions in neurons of the dentate gyrus and superficial layers of the frontal and temporal lobes.

Inclusion-body myositis (IBM) is a crippling disease usually found in people over age 50, in which muscle fibers develop inflammation and begin to atrophy—but in which the brain is spared and patients retain their full intellect. Two enzymes involved in the production of amyloid-β protein were found to be increased inside the muscle cells of patients with this most common, progressive muscle disease of older people, in which amyloid-β is also increased.

Another disease that is based on or associated with the accumulation and deposit of amyloid-like protein is macular degeneration. Macular degeneration is a common eye disease that causes deterioration of the macula, which is the central area of the retina (the paper-thin tissue at the back of the eye where light-sensitive cells send visual signals to the brain). Sharp, clear, "straight ahead" vision is processed by the macula. Damage to the macula results in the development of blind spots and blurred or distorted vision. Age-related macular degeneration (AMD) is a major cause of visual impairment in the United States and for people over age 65 it is the leading cause of legal blindness among Caucasians. Approximately 1.8 million Americans of age 40 and older have advanced AMD, and another 7.3 million people with intermediate AMD are at substantial risk for vision loss. The government estimates that by 2020 there will be 2.9 million people with advanced AMD. Victims of AMD are often surprised and frustrated to find out how little is known about the causes and treatment of this blinding condition.

There are two forms of macular degeneration: dry macular degeneration and wet macular degeneration. The dry form, in which the cells of the macula slowly begin to break down, is diagnosed in 85 percent of macular degeneration cases. Both eyes are usually affected by dry AMD, although one eye can lose vision while the other eye remains unaffected. Drusen, which are yellow deposits under the retina, are common early signs of dry AMD. The risk of developing advanced dry AMD or wet AMD increases as the number or size of the drusen increases. It is possible for dry AMD to advance and cause loss of vision without turning into the wet form of the disease; however, it is also possible for early-stage dry AMD to suddenly change into the wet form.

The wet form, although it only accounts for 15 percent of the cases, results in 90 percent of the blindness, and is considered advanced AMD (there is no early or intermediate stage of wet AMD). Wet AMD is always preceded by the dry form of the disease. As the dry form worsens, some people begin to have abnormal blood vessels growing behind the macula. These vessels are very fragile and will leak fluid and blood (hence 'wet' macular degeneration), causing rapid damage to the macula.

The dry form of AMD will initially often cause slightly blurred vision. The center of vision in particular may then become blurred and this region grows larger as the disease progresses. No symptoms may be noticed if only one eye is affected. In wet AMD, straight lines may appear wavy and central vision loss can occur rapidly.

Diagnosis of macular degeneration typically involves a dilated eye exam, visual acuity test, and a viewing of the back of the eye using a procedure called fundoscopy to help diagnose AMD, and—if wet AMD is suspected—fluorescein angiography may also be performed. If dry AMD reaches the advanced stages, there is no current treatment to prevent vision loss. However, a specific high dose formula of antioxidants and zinc may delay or prevent intermediate AMD from progressing to the advanced stage. Macugen® (pegaptanib sodium injection), laser photocoagulation and photodynamic therapy can control the abnormal blood vessel growth and bleeding in the macula, which is helpful for some people who have wet AMD; however, vision that is already lost will not be restored by these techniques. If vision is already lost, low vision aids exist that can help improve the quality of life.

One of the earliest signs of age-related macular degeneration (AMD) is the accumulation of extracellular deposits known as drusen between the basal lamina of the retinal pigmented epithelium (RPE) and Bruch's membrane (BM). Recent studies conducted by Anderson et al. have confirmed that drusen contain amyloid beta. (Experimental Eye Research 78 (2004) 243-256).

Pyroglutamated Aβ peptides have been shown to play a key role in accumulation of Aβ peptides and in plaque formation in Alzheimer's diseases. Due to their hydrophobic potential it has been shown that these peptides promote aggregation and plaque formation. It has further been shown in a transgenic mouse model expressing Aβ N3pE-42 in neurons that this peptide is neurotoxic in vivo and leads to loss of neurons (Wirths et al. (2009) Acta Neuropatho/118, 487-496).

Antibodies with specificities against the N-terminal pyroglutamate of Aβ peptides are believed to be advantageous because of their specificity towards only the pathogenic species of Aβ, which carry a pyroglutamate at the N-terminus, but not detecting APP or other Aβ species w/o the N-terminal pyroglutamate. It is thus believed that the risk of potential side effects, such as uncontrollable cerebral inflammation, will be reduced by use of the antibodies of the invention compared to antibodies directed to other Aβ species that the pyroglutamated variants.

Antibodies targeting Aβ N3pE peptides are known (Acero et al (2009) J Neuroimmunol 213, 39-46; Saido et al. (1996) Neuron 14, 457-466; U.S. Pat. No. 7,122,374 and WO 2012/136552).

However, there is a need for humanized and de-immunized antibodies with specificity for Aβ N3pE peptides that can be used in human treatment and that positively affect amyloidosis, in particular cognition in diseases and conditions where Aβ N3pE may be involved, such as clinical or pre-clinical Alzheimer's disease, Down's syndrome, and clinical or pre-clinical cerebral amyloid angiopathy.

The parental antibody of the antibody of the present invention is the clone #6 variant disclosed in WO 2017/009459, which has the light chain variable region with the amino acid sequence:

```
                                              (SEQ ID NO: 1)
DVVMTQSPLSLPVTLGQPASISCKSSQSLLYSDGKTYLNWFQQRPGQSPR

RLTYLVSKLDSGVPDRFSGSGSGTDFTLKISRVEAEDVGVYYCVQGTHFP

FTFGGGTKVEIK,
``` which is disclosed as SEQ ID NO: 14 in WO 2017/009459; and which has the heavy chain variable region with the amino acid sequence:

```
                                              (SEQ ID NO: 49)
QVQLVQSGAEVKKSGASVKVSCKASGYSFTGHTMNWVRQAPGQGLEWMGL

INPSNGVTRYNQKFQGRVTITRDTSTTTVHMELTSLTSEDTATYYCTREA

KREWDETYWGQGTLVTVSS;
``` which is disclosed as SEQ ID NO: 27 in WO 2017/009459.

However, with this clone #6 variant as disclosed in WO 2017/009459, it was not possible to establish a CMC manufacturing. In particular, and despite several attempts, no stable cell clones could be established in CHO-DG44 cells, only a weak transient expression (yielding insufficient antibody amounts) of this clone #6 variant was observed, and no stable expression, as a prerequisite for CMC manufacturing, could be established.

SUMMARY OF THE INVENTION

It was therefore the purpose of the invention to provide humanized and de-immunized antibodies with improved properties to overcome the disadvantages of the prior art antibodies.

In general, the invention provides novel methods and compositions comprising highly specific and highly effective antibodies, including chimeric antibodies and fragments thereof, including partially or fully humanized antibodies and fragments thereof, having the ability to specifically recognize and bind to specific epitopes from a range of β-amyloid antigens, in particular Aβ N3pE peptides, which may be presented to the antibody in a monomeric, dimeric, trimeric, etc, or a polymeric form, in form of an aggregate, fibers, filaments or in the condensed form of a plaque.

The purpose of the invention is in particular solved by an antibody or a functional variant thereof, wherein the variable part of the light chain of said antibody comprises, consists essentially of or consists of an amino acid sequence of:

```
                                              (SEQ ID NO: 1)
DVVMTQSPLSLPVTLGQPASISCKSSQSLLYSDGKTYLNWFQQRPGQSPR

RLTYLVSKLDSGVPDRFSGSGSGTDFTLKISRVEAEDVGVYYCVQGTHFP

FTFGGGTKVEIK,
``` and
wherein the variable part of heavy chain of said antibody comprises, consists essentially of or consists of an amino acid sequence of:

```
                                              (SEQ ID NO: 2)
QVQLVQSGAEVVKPGASVKVSCKASGYSFTGHTMNWVRQAPGQGLEWMGL

INPSDGVTRYNQKFQGRVTITRDTSTTTVHMELTSLTSEDTATYYCTREA

KREWDETYWGQGTLVTVSS.
```

The variable part of the heavy chain (SEQ ID NO: 2) contains three mutations at positions K12V, S14P and N55D compared to the parental antibody disclosed in WO 2017/009459.

Surprisingly, it was found that the introduction of these three point mutations led to a humanized and de-immunized antibody, which is capable for CMC manufacturing with high yields. It was possible to establish antibody producing cell lines in CHO-DG44 cells with the antibody of the invention comprising these three point mutations. It was further possible to establish an improved transient expression in CHO-DG44, resulting in higher yields of the antibody of the invention comprising K12V, S14P and N55D mutations compared to the parental antibody, while maintaining the favorable binding characteristics of the antibody. Finally, a stable expression could be established with the antibody of the invention comprising K12V, S14P and N55D mutations with high expression levels, enabling CMC production.

The invention provides humanized and de-immunized antibodies, or fragments thereof, that positively affect diseases and conditions of amyloidosis, where Aβ N3pE may be involved.

In another embodiment, the invention provides antibodies and fragments thereof that bind to Aβ N3pE peptides in the circulation and tissue, in particular in the brain. The antibodies of the invention are capable of binding free Aβ N3pE peptide molecules or even bound forms of Aβ N3pE peptides.

Thus, the present invention further provides antibodies that alter clearance of soluble and bound forms of Aβ N3pE peptides in the central nervous system, such as the brain, and the circulation, such as plasma.

In a further embodiment, the invention provides antibodies and fragments thereof, wherein the antibodies specifically bind to the pyroglutamate carrying N-terminus of Aβ N3pE.

In a further embodiment, the invention provides antibodies and fragments thereof, wherein the antibodies show an increased selectivity towards oligomers and/or fibrils of Aβ peptides. The antibodies of the present invention show a manifold, such as 10 times, 25 times, 50 times, 100 times, 150 times, 200 times, 250 times or more than 250 times lower binding constant ($K_D$ value) for binding to oligomers and/or fibrils of Aβ (1-42) than comparable monoclonal antibodies known in the prior art, in particular compared to the parental antibody disclosed in WO 2017/009459. Accordingly, the antibodies of the present invention, which were established to selectively bind to Aβ N3pE peptides, are more specific for Aβ N3pE peptides and show a decreased cross-reactivity against Aβ peptides other than Aβ N3pE.

In yet a further embodiment, the present invention also relates to the host cells transformed with the vectors or incorporating the nucleic acid molecules that express the antibodies of the invention or fragments thereof.

Moreover, the present invention provides pharmaceutical compositions comprising the antibodies of the invention and fragments thereof.

The invention further relates to the use of the antibodies of the invention and fragments thereof are useful for binding to and clearing or removing of Aβ N3pE in humans and thereby for diagnosing, preventing and treating diseases and conditions characterized by amyloidosis or Aβ N3pE toxicity.

In a particular embodiment, the antibodies of the invention, which are capable of binding to and clearing or removing of Aβ N3pE peptides in biological fluids and tissues, are useful for the prevention and/or treatment of conditions associated with the formation of Aβ N3pE-containing plaques, such as diffuse, neuritic, and cerebrovascular plaques in the brain.

The administration of the antibodies of the invention, including immunologically reactive fragments thereof, may lead to the clearance or removal of Aβ N3pE from the aforementioned plaques or other biological complexes. Thus, the antibody of the invention will readily be transport in the circulation, other body fluids and to sites where the aforementioned plaques and/or other biological complexes are formed or elsewhere where Aβ N3pE exhibits damaging effects.

In addition, removal of Aβ N3pE from plaques or other biological complexes by the antibodies of the invention may lead to the solubilization of insoluble forms of plaques and thus lead to the removal of complete plaques from the affected tissue, such as brain tissue. This, in turn, may lead to improvement of cognition in patients diagnosed with a neurodegenerative disease, such as mild cognitive impairment (MCI), Alzheimer's disease (AD), like for instance sporadic Alzheimer's disease (SAD) or Familial Alzheimer's dementias (FAD) like Familial British Dementia (FBD) and Familial Danish Dementia (FDD) or others, neurodegeneration in Down Syndrome, Lewy body dementia, hereditary cerebral hemorrhage with amyloidosis (Dutch type); the Guam Parkinson-Dementia complex. In particular, the present invention provides an antibody of the present invention for use in treatment of a condition selected from prodromal AD, mild AD, moderate AD and severe AD. In another embodiment, the present invention provides an antibody of the present invention for use in slowing cognitive decline in a patient diagnosed with a condition selected from clinical or pre-clinical Alzheimer's disease, Down's syndrome, and clinical or pre-clinical cerebral amyloid angiopathy.

The binding of the antibodies of the invention to Aβ N3pE in the circulation or other body fluids may further result to the removal of the circulating or soluble forms of Aβ N3pE. As discussed above, Aβ N3pE exhibits a high hydrophobicity and has a high affinity to other, e.g. nonpyroglutamated Aβ peptides, which results in the formation of oligomeric and supermolecular structures, such as amyloid plaques. It has been shown that in particular these oligomeric structures are highly neurotoxic. The formation of oligomeric structures leads to cell damage and death of neuronal cells. Thus, the removal of circulating or soluble forms of Aβ N3pE or even of oligomers comprising Aβ N3pE leads to the prevention of cell damage and/or neurotoxicity. Thus, the invention also provides methods of preventing of neurodegenerative disease, such as mild cognitive impairment (MCI), Alzheimer's disease (AD), like for instance sporadic Alzheimer's disease (SAD) or Familial Alzheimer's dementias (FAD) like Familial British Dementia (FBD) and Familial Danish Dementia (FDD) or others, neurodegeneration in Down Syndrome, Lewy body dementia, hereditary cerebral hemorrhage with amyloidosis (Dutch type), the Guam Parkinson-Dementia complex. In particular, the present invention provides methods of treatment of a condition selected from prodromal AD, mild AD, moderate AD and severe AD. In another embodiment, the present invention provides a method of slowing cognitive decline in a patient diagnosed with a condition selected from clinical or pre-clinical Alzheimer's disease, Down's syndrome, and clinical or pre-clinical cerebral amyloid angiopathy.

The invention further provides methods of preventing and/or treating of other diseases which are based on or associated with amyloid-like proteins, in particular Aβ N3pE, such as progressive supranuclear palsy, multiple sclerosis, Creutzfeld Jacob disease, Parkinson's disease, HIV-related dementia, ALS (amyotropic lateral sclerosis), dementia related to Adult Onset Diabetes; senile cardiac amyloidosis, and others, including macular degeneration.

The invention further provides a highly sensitive and concomitantly robust detection technique that allows quantitative determination of A variants, in particular Aβ N3pE, in biological samples, e.g. liquor or serum samples, preferably serum samples, or tissue samples. This is a tremendous challenge, taking the low abundance of these Aβ N3pE peptides in blood into account. Having such a detection technique available is, however, a prerequisite for studying efficacy of small molecule inhibitors in drug screening and drug development programs.

The antibodies enabled by the teaching of the present invention are particularly useful for diagnosis of amyloidosis, a group of diseases and disorders associated with amyloid plaque formation including secondary amyloidosis and age-related amyloidosis including, but not limited to, neurological disorders such as Alzheimer's Disease (AD), Lewy body dementia, Down's syndrome, hereditary cerebral hemorrhage with amyloidosis (Dutch type), the Guam Parkinson-Dementia complex, as well as other diseases which are based on or associated with amyloid-like proteins such as progressive supranuclear palsy, multiple sclerosis; Creutzfeld Jacob disease, hereditary cerebral hemorrhage with amyloidosis Dutch type, Parkinson's disease, HIV-related dementia, ALS (amyotropic lateral sclerosis), dementia related to Adult Onset Diabetes, senile cardiac amyloidosis, and others, including macular degeneration, to name just a few.

DETAILED DESCRIPTION OF THE INVENTION

Definitions

Figure 1:
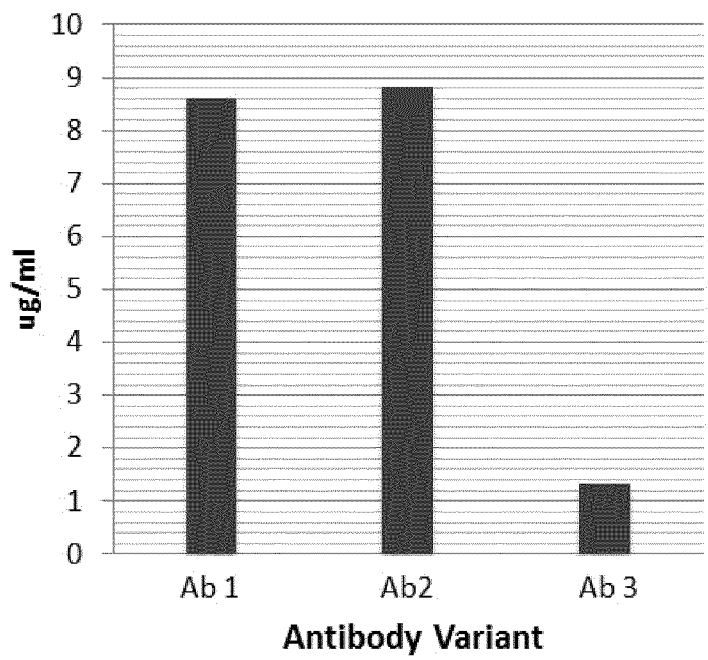
FIG. 1 shows the influence of the point mutations in the heavy chain on transient expression (A) and target binding (B) of individual variants of the antibody of the invention. All antibodies tested contain the variable part of the light chain of SEQ ID NO. 1 and the K324A mutation in the heavy chain.
- Ab 1: contains the two mutations K12V and S14P in the variable part of the heavy chain compared to the parental sequence SEQ ID NO: 49;
- Ab 2: contains the mutation N55D in the variable part of the heavy chain compared to the parental sequence SEQ ID NO: 49;
- Ab 3: represents the parental sequence SEQ ID NO: 49 of the variable part of the heavy chain w/o any mutations.
Figure 1:
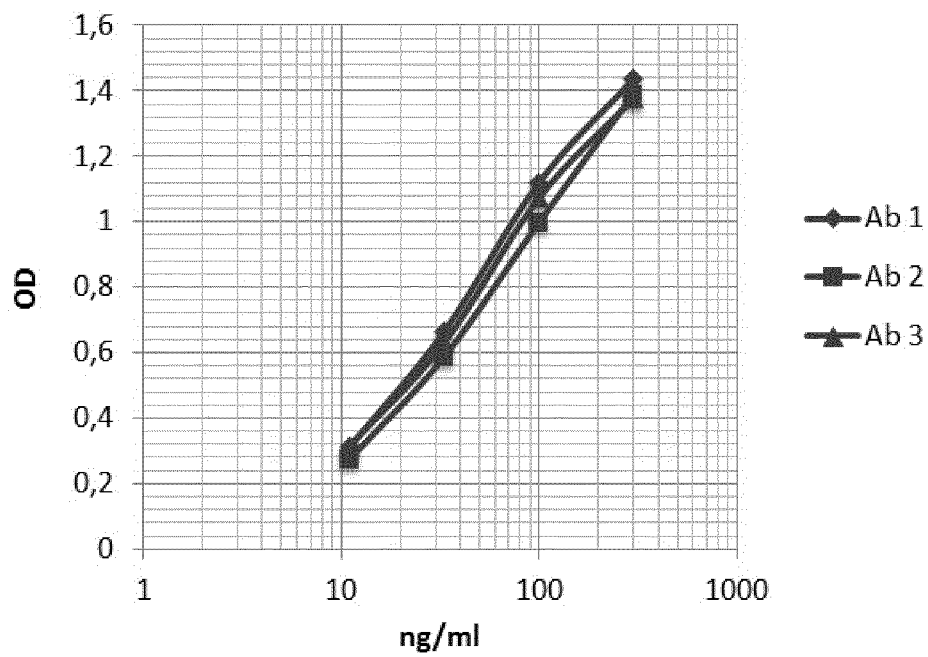

The term "antibody" is used in the broadest sense and specifically covers intact monoclonal antibodies, polyclonal antibodies, multispecific antibodies (e.g. bispecific antibodies) formed from at least two intact antibodies, and antibody fragments so long as they exhibit the desired biological activity. The antibody may be an IgM, IgG (e.g. IgG1, IgG2, IgG3 or IgG4), IgD, IgA or IgE, for example. Preferably however, the antibody is not an IgM antibody.

"Antibody fragments" comprise a portion of an intact antibody, generally the antigen binding or variable region of the intact antibody. Examples of antibody fragments include Fab, Fab', F(ab')2, and Fv fragments: diabodies; single-chain antibody molecules; and multispecific antibodies formed from antibody fragments.

The term "monoclonal antibody" as used herein refers to an antibody obtained from a population of substantially homogeneous antibodies, i.e. the individual antibodies comprising the population are identical except for possible naturally occurring mutations that may be present in minor amounts. Monoclonal antibodies are highly specific, being directed against a single antigenic site. Furthermore, in contrast to "polyclonal antibody" preparations which typically include different antibodies directed against different determinants (epitopes), each monoclonal antibody is directed against a single determinant on the antigen. In addition to their specificity, the monoclonal antibodies can frequently be advantageous in that they are synthesized by the hybridoma culture, uncontaminated by other immunoglobulins. The "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Köhler et al., Nature, 256:495 (1975), or may be made by generally well known recombinant DNA methods. The "monoclonal antibodies" may also be isolated from phage antibody libraries using the techniques described in Clackson et al., Nature, 352:624-628 (1991) and Marks et al., J. Mol. Biol., 222:581-597 (1991), for example.

The monoclonal antibodies herein specifically include chimeric antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity.

"Humanized" forms of non-human (e.g., murine) antibodies are immunoglobulins, immunoglobulin chains or fragments thereof (such as Fv, Fab, Fab', F(ab')2 or other antigen-binding subsequences of antibodies) which contain a minimal sequence derived from a non-human immunoglobulin. For the most part, humanized antibodies are human immunoglobulins (recipient antibody) in which residues from a complementarity-determining region (CDR) of the recipient are replaced by residues from a CDR of a non-human species (donor antibody) such as mouse, rat or rabbit having the desired specificity, affinity, and capacity. In some instances, Fv framework region (FR) residues of the human immunoglobulin are replaced by corresponding non-human residues. Furthermore, humanized antibodies may comprise residues which are found neither in the recipient antibody nor in the imported CDR or framework sequences.

These modifications are made to further refine and optimize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin sequence. The humanized antibody optimally also will comprise at least a portion of an immunoglobulin constant region (Fc), typically that of a human immunoglobulin. For further details, see Jones et al., Nature, 321:522-525 (1986), Reichmann et al, Nature. 332:323-329 (1988): and Presta, Curr. Op. Struct. Biel., 2:593-596 (1992).

In addition to "humanization", "de-immunization" includes other changes such as removing T cell epitopes.

The term "therapeutically effective amount" as used herein and in the appended claims means that the amount of antibody administered is of sufficient guantity to achieve the intended purpose such as, in this case, at least the removal of circulating or soluble forms of pyroglutamated amyloid beta (Aβ N3pE) peptide and variants thereof, but preferably the clearance or removal of Aβ N3pE peptide from plaques or other biological complexes. Or more preferably the reduction of the plaque load and/or the removal of complete plaques from the affected tissue, such as brain tissue.

"Single-chain Fv" or "sFv" antibody fragments comprise the $V_H$ and $V_L$ domains of antibody, wherein these domains are present in a single polypeptide chain. Generally, the Fv polypeptide further comprises a polypeptide linker between the $V_H$ and $V_L$ domains which enables the sFv to form the desired structure for antigen binding. For a review of sFv see Plckthun in The Pharmacology of Monoclonal Antibodies, vol. 113, Rosenburg and Moore eds., Springer-Verlag, New York, pp. 269-315 (1994).

The term "diabodies" refers to small antibody fragments with two antigen-binding sites, which fragments comprise a heavy-chain variable domain ($V_H$) connected to a light-chain variable domain ($V_D$) in the same polypeptide chain ($V_H$-$V_D$). By using a linker that is too short to allow pairing between the two domains on the same chain, the domains are forced to pair with the complementary domains of another chain and create two antigen-binding sites. Diabodies are described more fully in Hollinger et al., Proc. Natl. Acad. Sol. USA, 90:6444-6448 (1993).

An "isolated" antibody is one which has been identified and separated and/or recovered from a component of its natural environment. Contaminant components of its natural environment are materials which would interfere with diagnostic or therapeutic uses for the antibody, and may include enzymes, hormones, and other proteinaceous or non-proteinaceous solutes. In preferred embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

As used herein, the expressions "cell", "cell line," and "cell culture" are used interchangeably and all such designations include progeny. Thus, the words "transformants" and "transformed cells" include the primary subject cell and culture derived therefrom without regard for the number of transfers. It is also understood that all progeny may not be precisely identical in DNA content, due to deliberate or inadvertent mutations. Mutant progeny that have the same function or biological activity as screened for in the originally transformed cell are included. Where distinct designations are intended, this will be clear from the context.

The terms "polypeptide", "peptide", and "protein", as used herein, are interchangeable and are defined to mean a biomolecule composed of amino acids linked by a peptide bond.

If peptide or amino acid sequences are mentioned herein, each amino acid residue is represented by a one-letter or a three-letter designation, corresponding to the trivial name of the amino acid, in accordance with the following conventional list:

| Amino Acid | One-Letter Symbol | Three-Letter Symbol |
|---|---|---|
| Alanine | A | Ala |
| Arginine | R | Arg |
| Asparagine | N | Asn |
| Aspartic acid | D | Asp |
| Cysteine | C | Cys |
| Glutamine | Q | Gln |
| Glutamic acid | E | Glu |
| Glycine | G | Gly |
| Histidine | H | His |
| Isoleucine | I | Ile |
| Leucine | L | Leu |
| Lysine | K | Lys |
| Methionine | M | Met |
| Phenylalanine | F | Phe |
| Proline | P | Pro |
| Serine | S | Ser |
| Threonine | T | Thr |
| Tryptophan | W | Trp |
| Tyrosine | Y | Tyr |
| Valine | V | Val |

The terms "a", "an" and "the" as used herein are defined to mean "one or more" and include the plural unless the context is inappropriate.

The language "diseases and disorders which are caused by or associated with amyloid or amyloid-like proteins" includes, but is not limited to, diseases and disorders caused by the presence or activity of amyloid-like proteins in monomeric, fibril, or polymeric state, or any combination of the three. Such diseases and disorders include, but are not limited to, amyloidosis, endocrine tumors, and macular degeneration.

The term "amyloidosis" refers to a group of diseases and disorders associated with amyloid plaque formation including, but not limited to, secondary amyloidosis and age-related amyloidosis such as diseases including, but not limited to, neurological disorders such as Alzheimer's Disease (AD), including diseases or conditions characterized by a loss of cognitive memory capacity such as, for example, mild cognitive impairment (MCI), sporadic Alzheimer's disease, Lewy body dementia, Down's syndrome, hereditary cerebral hemorrhage with amyloidosis (Dutch type); the Guam Parkinson-Dementia complex, familial forms of Alzheimer's disease like Familial British Dementia (FBD) and Familial Danish Dementia (FDD); as well as other diseases which are based on or associated with amyloid-like proteins such as progressive supranuclear palsy, multiple sclerosis; Creutzfeld Jacob disease, Parkinson's disease, HIV-related dementia, ALS (amyotropic lateral sclerosis), inclusion-body myositis (IBM), Adult Onset Diabetes, and senile cardiac amyloidosis; and various eye diseases including macular degeneration, drusen-related optic neuropathy, and cataract due to beta-amyloid deposition.

"Amyloid R, Aβ or/β-amyloid" is an art recognized term and refers to amyloid β proteins and peptides, amyloid β precursor protein (APP), as well as modifications, fragments and any functional equivalents thereof. In particular, by amyloid β as used herein is meant any fragment produced by proteolytic cleavage of APP but especially those fragments which are involved in or associated with the amyloid pathologies including, but not limited to, $A\beta_{1-38}$, $A\beta_{1-40}$, $A\beta_{1-42}$. The amino acid sequences of these Aβ peptides are as follows:

Aβ 1-42 (SEQ ID NO. 37):
Asp-Ala-Glu-Phe-Arg-His-Asp-Ser-Gly-Tyr-Glu-Val-

His-His-Gln-Lys-Leu-Val-Phe-Phe-Ala-Glu-Asp-Val-

Gly-Ser-Asn-Lys-Gly-Ala-Ile-Ile-Gly-Leu-Met-Val-

Gly-Gly-Val-Val-Ile-Ala

Aβ 1-40 (SEQ ID NO. 38):
Asp-Ala-Glu-Phe-Arg-His-Asp-Ser-Gly-Tyr-Glu-Val-

His-His-Gln-Lys-Leu-Val-Phe-Phe-Ala-Glu-Asp-Val-

Gly-Ser-Asn-Lys-Gly-Ala-Ile-Ile-Gly-Leu-Met-Val-

Gly-Gly-Val-Val

Aβ 1-38 (SEQ ID NO. 39):
Asp-Ala-Glu-Phe-Arg-His-Asp-Ser-Gly-Tyr-Glu-Val-

His-His-Gln-Lys-Leu-Val-Phe-Phe-Ala-Glu-Asp-Val-

Gly-Ser-Asn-Lys-Gly-Ala-Ile-Ile-Gly-Leu-Met-Val-

Gly-Gly

"pGlu-Aβ" or "Aβ N3pE" refers to N-terminally truncated forms of Aβ, that start at the glutamic acid residue at position 3 in the amino acid sequence of Aβ, and wherein said glutamic acid residue is cyclized to form a pyroglutamic acid residue. In particular, by pGlu-Aβ or Aβ N3pE as used herein are meant those fragments which are involved in or associated with the amyloid pathologies including, but not limited to, $pGlu-A\beta_{3-38}$, $pGlu-A\beta_{3-40}$, $p-Glu-A\beta_{3-42}$.

The sequences of the N-terminally truncated forms of Aβ, $A\beta_{3-38}$, $A\beta_{3-40}$, $A\beta_{3-42}$ are as follows:

Aβ 3-42 (SEQ ID NO. 40):
Glu-Phe-Arg-His-Asp-Ser-Gly-Tyr-Glu-Val-His-His-

Gln-Lys-Leu-Val-Phe-Phe-Ala-Glu-Asp-Val-Gly-Ser-

```
Asn-Lys-Gly-Ala-Ile-Ile-Gly-Leu-Met-Val-Gly-Gly-

Val-Val-Ile-Ala

Aβ 3-40 (SEQ ID NO. 41):
Glu-Phe-Arg-His-Asp-Ser-Gly-Tyr-Glu-Val-His-His-

Gln-Lys-Leu-Val-Phe-Phe-Ala-Glu-Asp-Val-Gly-Ser-

Asn-Lys-Gly-Ala-Ile-Ile-Gly-Leu-Met-Val-Gly-Gly-

Val-Val

Aβ 3-38 (SEQ ID NO. 42):
Glu-Phe-Arg-His-Asp-Ser-Gly-Tyr-Glu-Val-His-His-

Gln-Lys-Leu-Val-Phe-Phe-Ala-Glu-Asp-Val-Gly-Ser-

Asn-Lys-Gly-Ala-Ile-Ile-Gly-Leu-Met-Val-Gly-Gly
```

The present invention pertains to antibodies specific for human A peptides that are N-terminally truncated by cleaving off or loosing amino acids no. 1 and 2 of the N-terminus and in which the so uncovered N-terminal amino acid no. 3 is modified by pyroglutamate formation and which thus bear a pyroglutamate residue at position 3 of the N-terminus (further referred to as Aβ N3pE peptides or N3pE-Aβ peptides or pyroglutamated A peptides).

In a first aspect, the present invention pertains to an antibody, wherein the variable part of the light chain of said antibody comprises, consists essentially of or consists of an amino acid sequence of:

```
                                          (SEQ ID NO: 1)
DVVMTQSPLSLPVTLGQPASISCKSSQSLLYSDGKTYLNWFQQRPGQS

PRRLTYLVSKLDSGVPDRFSGSGSGTDFTLKISRVEAEDVGVYYCVQG

THFPFTFGGGTKVEIK,
``` and
wherein the variable part of heavy chain of said antibody comprises, consists essentially of or consists of an amino acid sequence of:

```
                                          (SEQ ID NO: 2)
QVQLVQSGAEVVKPGASVKVSCKASGYSFTGHTMNWVRQAPGQGLEWM

GLINPSDGVTRYNQKFQGRVTITRDTSTTTVHMELTSLTSEDTATYYC

TREAKREWDETYWGQGTLVTVSS
```

In a preferred embodiment of the present invention, the antibody having the variable part of the light chain of said antibody, which comprises, consists essentially of or consists of the amino acid sequence of SEQ ID NO: 1, comprises the following CDR regions in the light chain:

```
V_L CDR1:
                                          (SEQ ID NO: 3)
SSQSLLYSDGKTYLN;

V_L CDR2:
                                          (SEQ ID NO: 4)
LVSKLDS;
and

V_L CDR3:
                                          (SEQ ID NO: 5)
VQGTHFP.
```

In a further preferred embodiment of the present invention, the antibody having the variable part of the heavy chain of said antibody, which comprises, consists essentially of or consists of the amino acid sequence of SEQ ID NO: 2, comprises the following CDR regions in the heavy chain:

```
V_H CDR1:
                                          (SEQ ID NO: 6)
GYSFTGHTMN;

V_H CDR2:
                                          (SEQ ID NO: 7)
LINPSDGVTRYNQKFQG;
and V_H CDR3:
                                          (SEQ ID NO: 8)
EAKREWDETY.
```

The invention further provides the light chains and the heavy chains of the antibody of the invention.

In a preferred embodiment, the antibody of the invention has a light chain, wherein the light chain comprises, consists essentially of or consists of the amino acid sequence of:

```
                                         (SEQ ID NO: 17)
DVVMTQSPLSLPVTLGQPASISCKSSQSLLYSDGKTYLNWFQQRPG

QSPRRLTYLVSKLDSGVPDRFSGSGSGTDFTLKISRVEAEDVGVYY

CVQGTHFPFTFGGGTKVEIKRTVAAPSVFIFPPSDEQLKSGTASVV

CLLNNFYPREAKVQWKVDNALQSGNSQESVTEQDSKDSTYSLSSTL

TLSKADYEKHKVYACEVTHQGLSSPVTKSFNRGEC.
```

In a further preferred embodiment, the antibody of the invention has a heavy chain, wherein the heavy chain comprises, consists essentially of or consists of the amino acid sequence of:

```
                                         (SEQ ID NO: 19)
QVQLVQSGAEVVKPGASVKVSCKASGYSFTGHTMNWVRQAPGQGLEW

MGLINPSDGVTRYNQKFQGRVTITRDTSTTTVHMELTSLTSEDTATY

YCTREAKREWDETYWGQGTLVTVSSASTKGPSVFPLAPSSKSTSGGT

AALGCLVKDYFPEPVTVSWNSGALTSGVHTFPAVLQSSGLYSLSSVV

TVPSSSLGTQTYICNVNHKPSNTKVDKKVEPKSCDKTHTCPPCPAPE

LLGGPSVFLFPPKPKDTLMISRTPEVTCVVVDVSHEDPEVKFNWYVD

GVEVHNAKTKPREEQYNSTYRVVSVLTVLHQDWLNGKEYKCKVSNKA

LPAPIEKTISKAKGQPREPQVYTLPPSRDELTKNQVSLTCLVKGFYP

SDIAVEWESNGQPENNYKTTPPVLDSDGSFFLYSKLTVDKSRWQQGN

VFSCSVMHEALHNHYTQKSLSLSPGK.
```

C1q and two serine proteases, C1r and C1s, form the complex C1, the first component of the complement dependent cytotoxicity (CDC) pathway. C1q is a hexavalent molecule with a molecular weight of approximately 460,000 and a structure likened to a bouquet of tulips in which six collagenous "stalks" are connected to six globular head regions (Burton and Woof, Advances in Immunol 51:1-84; 1992). Binding of IgG1 molecules to C1q initiates complement activation and subsequently leads to complement-mediated cell lysis. The antibodies of the present invention shall be used in treatment of inflammatory diseases and conditions, i.e. the antibodies of the present invention shall have anti-inflammatory properties.

Effector functions of the antibodies of the invention can also be mediated by the interaction of the Fc region of an antibody with Fc receptors (FcRs), which are specialized cell surface receptors on hematopoietic cells. Fc receptors belong to the immunoglobulin superfamily, and have been shown to mediate both the removal of antibody-coated pathogens by phagocytosis of immune complexes, and the lysing of erythrocytes and various other cellular targets (e.g. tumor cells) coated with the corresponding antibody, via antibody dependent cell mediated cytotoxicity (ADCC) (Van de Winkel and Anderson, J. Leuk. Biol. 49:511-24; 1991).

Therefore, the present invention further provides antibodies that still bind to the Fc receptors to fulfill their effector functions. But, preferably the antibodies of the invention do not show a complement dependent cytotoxicity. More preferably, the antibodies of the invention do not activate the complement system, but rather inhibit the complement-mediated cell lysis.

Thus, in a preferred embodiment, the antibodies of the present invention have a human IgG Fc region, which comprises one or more an amino acid substitutions, preferably the substitution of 3 or 2 amino acids, most preferably the substitution of one amino acid. The amino acid substitutions can be achieved by conventional methods, such as site-directed mutagenesis of the human IgG1 Fc region of the antibodies of the present invention.

In a more preferred embodiment, the antibodies of the present invention have a human IgG Fc region which comprises an amino acid substitution at position 324 as shown in SEQ ID NO: 18 [position 324 corresponds to position 322 according to EU numbering scheme, Kabat et al., Sequences of Proteins of Immunological Interest, 5th Ed., US Department of Health and Human Services, NIH Publication No. 91-3242, National Institutes of Health, Bethesda, MD (1991); Edelman et al., PNAS USA 63:78-85 (1969)]. The amino acid substitution is preferably K324A.

In a most preferred embodiment, the antibody of the present invention has a heavy chain, which comprises, consists essentially of or consists of an amino acid sequence:

(SEQ ID NO: 18)
QVQLVQSGAEVVKPGASVKVSCKASGYSFTGHTMNWVRQAPGQGLEWM

GLINPSDGVTRYNQKFQGRVTITRDTSTTTVHMELTSLTSEDTATYYC

TREAKREWDETYWGQGTLVTVSSASTKGPSVFPLAPSSKSTSGGTAAL

GCLVKDYFPEPVTVSWNSGALTSGVHTFPAVLQSSGLYSLSSVVTVPS

SSLGTQTYICNVNHKPSNTKVDKKVEPKSCDKTHTCPPCPAPELLGGP

SVFLFPPKPKDTLMISRTPEVTCVVVDVSHEDPEVKFNWYVDGVEVHN

AKTKPREEQYNSTYRVVSVLTVLHQDWLNGKEYKCAVSNKALPAPIEK

TISKAKGQPREPQVYTLPPSRDELTKNQVSLTCLVKGFYPSDIAVEWE

SNGQPENNYKTTPPVLDSDGSFFLYSKLTVDKSRWQQGNVFSCSVMHE

ALHNHYTQKSLSLSPGK.

Further according the invention, the antibodies comprising, essentially consisting of or consisting of the following combinations of the variable parts of the light chain and heavy chain and the light chain and the heavy chain are preferred:

A) Light chain variable part: SEQ ID NO: 1
  Heavy chain variable part: SEQ ID NO: 2
  Light chain: SEQ ID NO: 17
  Heavy chain: SEQ ID NO: 19

B) Light chain variable part: SEQ ID NO: 1
  Heavy chain variable part: SEQ ID NO: 2
  Light chain: SEQ ID NO: 17
  Heavy chain: SEQ ID NO: 18

Antibody according B) is most preferred. The heavy chain contains the K324A amino acid exchange.

Preferred antibodies according to the invention are humanized forms of monoclonal mouse antibodies that are produced by hybridoma cell line Aβ 6-1-6 (Deposit No. DSM ACC 2924), which is described in WO 2010/009987.

The sequences of the light and heavy chains for the antibodies of the present invention can vary. The immunoglobulins can have two pairs of light chain/heavy chain complexes, at least one chain comprising one or more mouse complementarity determining regions (CDRs) functionally joined to human framework region segments.

In a preferred embodiment, the antibody of the invention comprises two light chains and two heavy chains, wherein the amino acid sequence of each light chain is SEQ ID NO:17, and the amino acid sequence of each heavy chain is SEQ ID NO: 18 or SEQ ID NO: 19.

More preferably, the antibody of the invention comprises two light chains and two heavy chains, wherein the amino acid sequence of each light chain is SEQ ID NO:17, and the amino acid sequence of each heavy chain is SEQ ID NO: 19.

Most preferably, the antibody of the invention comprises two light chains and two heavy chains, wherein the amino acid sequence of each light chain is SEQ ID NO:17, and the amino acid sequence of each heavy chain is SEQ ID NO: 18.

In another embodiment, the present invention is directed to recombinant nucleic acid molecules encoding the antibodies of the invention comprising the heavy and light chain CDRs as set forth herein.

The human framework region of the antibodies of the invention is determined by comparison of a framework or variable region amino acid sequence of a CDR-providing non-human immunoglobulin with corresponding sequences in a sequence collection comprising human immunoglobulin variable regions. A sequence having a high percentage of identical amino acids is selected.

In a preferred embodiment of the invention, the variable part of the light chain having the amino acid sequence according to SEQ ID NO: 1 is encoded by a nucleic acid molecule which comprises, consists essentially of or consists of the nucleic acid sequence of:

(SEQ ID NO: 9)
Gacgtggtgatgactcagtctccactctccctgcccgtcacccttgga cagccggcctccatctcctgcaagtcaagtcagagcctcctgcactcc gacggcaagacctacttgaactggttccagcagaggccaggccagtct ccaaggcgcctgacctatctggtgtctaagctggactctggggtccca gacagattcagcggcagtgggtcaggcactgacttcacactgaagatc agcagggtggaggctgaggatgtcggagtctactactgcgtgcaaggt acacacttcccattcacgttcggcggagggaccaaggtggaaatcaaa.

In a further preferred embodiment of the invention, the variable part of the heavy chain having the amino acid sequence according to SEQ ID NO: 2 is encoded by a nucleic acid molecule which comprises, consists essentially of or consists of the nucleic acid sequence of:

```
                                    (SEQ ID NO: 10)
caggtgcagctcgtgcagtctggggctgaggtggtgaagccaggtgcct cagtgaaggtctcctgcaaggcatctggttactcattcactggtcacac catgaactgggtgcgacaggcccctggacaagggcttgagtggatggga ctcatcaatccttccgatggtgttactaggtacaaccagaagttccagg gcagagtcaccatcaccagggacacgtccacgaccaccgttcacatgga gctgaccagcctgacatctgaggacacggccacctactactgtacgaga gaggcgaaacgggagtgggacgagacttactggggcagggaaccctgg tcaccgtctcctca.
```

In a further preferred embodiment of the invention, the CDR regions of the light chain of the antibody of the invention are encoded by a nucleic acid molecule having the nucleic acid sequence:

```
V_L CDR1:
                                    (SEQ ID NO: 11)
tcaagtcagagcctcctgcactccgacggcaagacctacttgaac;

V_L CDR2:
                                    (SEQ ID NO: 12)
ctggtgtctaagctggactct;
and V_L CDR3:
                                    (SEQ ID NO: 13)
gtgcaaggtacacacttccca.
```

In a further preferred embodiment of the invention, the CDR regions of the heavy chain of the antibody of the invention are encoded by a nucleic acid molecule having the nucleic acid sequence:

```
V_H CDR1:
                                    (SEQ ID NO: 14)
ggttactcattcactggtcacaccatgaac;

V_H CDR2:
                                    (SEQ ID NO: 15)
ctcatcaatccttccgatggtgttactaggtacaaccagaagttcc Agggc;
and V_H CDR3:
                                    (SEQ ID NO: 16)
gaggcgaaacgggagtgggacgagacttac.
```

In a further preferred embodiment of the invention, the light chain is encoded by a nucleic acid molecule which comprises, consists essentially of or consists of the amino acid sequence of:

```
                                    (SEQ ID NO: 20)
Gacgtggtgatgactcagtctccactctccctgcccgtcacccttgg acagccggcctccatctcctgcaagtcaagtcagagcctcctgcact ccgacggcaagacctacttgaactggttccagcagaggccaggccag tctccaaggcgcctgacctatctggtgtctaagctggactctggggt cccagacagattcagcggcagtgggtcaggcactgacttcacactga agatcagcagggtggaggctgaggatgtcggagtctactactgcgtg caaggtacacacttcccattcacgttcggcggagggaccaaggtgga
```

```
aatcaaaaggaccgtggccgcaccctctgtgttcatcttcccccca gcgacgagcagctgaagagcggcactgcatctgtcgtgtgtctgctg aacaacttctacccaagggaggcgaaagtgcagtggaaggtagacaa cgccttgcaatccggcaactcccaggagagcgtgaccgagcaggaca gcaaagactcaacctacagcctgagcagtactttgaccctgtctaag gccgattacgagaagcacaaggtgtacgcctgcgaggtaacccacca gggactgagctctcccgtgaccaagagcttcaacaggggcgagtgc.
```

In a further preferred embodiment of the invention, the heavy chain is encoded by a nucleic acid molecule which comprises, consists essentially of or consists of the amino acid sequence of:

```
                                    (SEQ ID NO: 21)
caggtgcagctcgtgcagtctggggctgaggtggtgaagccaggtgcctc agtgaaggtctcctgcaaggcatctggttactcattcactggtcacacca tgaactgggtgcgacaggcccctggacaagggcttgagtggatgggactc atcaatccttccgatggtgttactaggtacaaccagaagttccagggcag agtcaccatcaccagggacacgtccacgaccaccgttcacatggagctga ccagcctgacatctgaggacacggccacctactactgtacgagagaggcg aaacgggagtgggacgagacttactggggcagggaaccctggtcaccgt ctcctcagccagcactaagggcccgagcgtgttcccctcgccctagca gtaagagcaccagcggtggcacggcggcacttggctgcttggttaaggac tacttcccagagcccgtgaccgtgtcctggaactctggggcacttaccag tggcgtgcacaccttcccgctgtactgcagagcagcggcttgtacagct tgtcttccgtcgtaacggtgcccagcagcagcttgggaacccagacctac atctgcaacgtaaaccacaagccatccaacaccaaggtagacaaaaaggt cgaacccaagtcctgcgacaagacccacacctgtccaccctgtcctgcac ccgagctcctgggaggtcccagcgttttcctgttccctccaaagccaaag gataccctgatgatcagcaggaccccgaggtgacctgcgtggtggtgga cgtgagccacgaagaccctgaggtcaagttcaactggtacgttgatgggg tggaggtacacaatgccaagaccaaacctcgagaggagcaatacaacagc acctaccgagttgtgagcgtgcttaccgtgctgcaccaggactggctgaa cggcaaggagtacaagtgcgctgtgagcaacaaggctctgccggctccca tcgagaagaccatcagcaaggccaagggccagcccagggagccacaggtt tacacgttgccccctcaagggacgagttgaccaagaaccaggtttccct cacgtgccttgtgaagggcttctaccccagcgacatcgccgtggaatggg agagcaacgggcagcccgagaacaactacaagacgaccccccctgttctg gacagcgacggctcttctttcctgtattcaaagctcaccgtggacaaaag caggtggcagcagggtaatgtgttcctgcagcgtgatgcacgaggccc tgcataaccactacacccaaaagagcttgagcctctcccccggtaag.
```

In a further preferred embodiment of the invention, the heavy chain is encoded by a nucleic acid molecule which comprises, consists essentially of or consists of the amino acid sequence of:

(SEQ ID NO: 22)
caggtgcagctcgtgcagtctggggctgaggtggtgaagccaggtgcctc agtgaaggtctcctgcaaggcatctggttactcattcactggtcacacca tgaactgggtgcgacaggcccctggacaagggcttgagtggatgggactc atcaatccttccgatggtgttactaggtacaaccagaagttccagggcag agtcaccatcaccagggacacgtccacgaccaccgttcacatggagctga ccagcctgacatctgaggacacggccacctactactgtacgagagaggcg aaacgggagtgggacgagacttactggggcagggaaccctggtcaccgt ctcctcagccagcactaagggcccgagcgtgttcccctcgcccctagca gtaagagcaccagcggtggcacggcggcacttggctgcttggttaaggac tacttcccagagcccgtgaccgtgtcctggaactctggggcacttaccag tggcgtgcacaccttccccgctgtactgcagagcagcggcttgtacagct tgtcttccgtcgtaacggtgcccagcagcagcttgggaacccagacctac atctgcaacgtaaaccacaagccatccaacaccaaggtagacaaaaaggt cgaacccaagtcctgcgacaagacccacacctgtccaccctgtcctgcac ccgagctcctgggaggtcccagcgttttcctgttccctccaaagccaaag gataccctgatgatcagcaggaccccgaggtgacctgcgtggtggtgga cgtgagccacgaagaccctgaggtcaagttcaactggtacgttgatgggg tggaggtacacaatgccaagaccaaacctcgagaggagcaatacaacagc acctaccgagttgtgagcgtgcttaccgtgctgcaccaggactggctgaa cggcaaggagtacaagtgcaaggtgagcaacaaggctctgccggctccca tcgagaagaccatcagcaaggccaagggccagcccagggagccacaggtt tacacgttgccccctcaagggacgagttgaccaagaaccaggtttccct cacgtgccttgtgaagggcttctaccccagcgacatcgccgtggaatggg agagcaacgggcagcccgagaacaactacaagacgacccccctgttctg gacagcgacggctctttcttcctgtattcaaagctcaccgttggacaaaag caggtggcagcagggtaatgtgttctcctgcagcgtgatgcacgaggccc tgcataaccactacacccaaaagagcttgagcctctccccggtaag Further according the invention, antibodies are preferred, which are encoded by combination of nucleic acid molecules comprising, essentially consisting of or consisting of:

C) Light chain variable part: SEQ ID NO: 9
  Heavy chain variable part: SEQ ID NO: 10
  Light chain: SEQ ID NO: 20
  Heavy chain: SEQ ID NO: 22
D) Light chain variable part: SEQ ID NO: 9
  Heavy chain variable part: SEQ ID NO: 10
  Light chain: SEQ ID NO: 20
  Heavy chain: SEQ ID NO: 21

Combination D) is most preferred since it encodes for a humanized and de-immunized antibody which contains the K324A amino acid exchange in the heavy chain.

The aforementioned nucleic acid molecules can be integrated into expression vectors well known in the art. Transfection of these expression vectors in an appropriate host, the selection of the host as well as the expression collection and purification of the light chains, heavy chains, light/heavy chain dimers or intact antibodies, binding fragments or other immunoglobulin forms are well-known procedures in the art.

One skilled in the art can select a vector based on desired properties, for example, for production of a vector in a particular cell such as a mammalian cell or a bacterial cell.

Any of a variety of inducible promoters or enhancers can be included in the vector for expression of an antibody of the invention or nucleic acid that can be regulated. Such inducible systems, include, for example, tetracycline inducible System (Gossen & Bizard, Proc. Natl. Acad. Sci. USA, 89:5547-5551 (1992); Gossen et al., Science, 268:17664769 (1995); Clontech, Palo Alto, Calif.); metallothionein promoter induced by heavy metals; insect steroid hormone responsive to ecdysone or related steroids such as muristerone (No et al., Proc. Natl. Acad. Sci. USA, 93:3346-3351 (1996); Yao et al., Nature, 366:476-479 (1993); Invitrogen, Carlsbad, Calif.); mouse mammary tumor virus (MMTV) induced by steroids such as glucocorticoid and estrogen (Lee et al., Nature, 294:228-232 (1981); and heat shock promoters inducible by temperature changes; the rat neuron specific enolase gene promoter (Forss-Petter, et al., Neuron 5; 197-197 (1990)); the human β-actin gene promoter (Ray, et al., Genes and Development (1991) 5:2265-2273); the human platelet derived growth factor B (PDGF-B) chain gene promoter (Sasahara, et al., Cell (1991) 64:217-227); the rat sodium channel gene promoter (Maue, et al., Neuron (1990) 4:223-231); the human copper-zinc superoxide dismutase gene promoter (Ceballos-Picot, et al., Brain Res. (1991) 552:198-214); and promoters for members of the mammalian POU-domain regulatory gene family (Xi et al., (1989) Nature 340:35-42).

Regulatory elements, including promoters or enhancers, can be constitutive or regulated, depending upon the nature of the regulation. The regulatory sequences or regulatory elements are operatively linked to one of the nucleic acid molecule sequences of the invention such that the physical and functional relationship between the nucleic acid molecule sequence and the regulatory sequence allows transcription of the nucleic acid molecule sequence. Vectors useful for expression in eukaryotic cells can include, for example, regulatory elements including the CAG promoter, the SV40 early promoter, the cytomegalovirus (CMV) promoter, the mouse mammary tumor virus (MMTV) steroid-inducible promoter, Pgtf, Moloney marine leukemia virus (MMLV) promoter, thy-1 promoter and the like.

If desired, the vector can contain a selectable marker. As used herein, a "selectable marker" refers to a genetic element that provides a selectable phenotype to a cell in which the selectable marker has been introduced. A selectable marker is generally a gene whose gene product provides resistance to an agent that inhibits cell growth or kills a cell. A variety of selectable markers can be used in the DNA constructs of the invention, including, for example, Neo, Hyg, hisD, Gpt and Ble genes, as described, for example in Ausubel et al. (Current Protocols in Molecular Biology (Supplement 47), John Wiley & Sons, New York (1999)) and U.S. Pat. No. 5,981,830. Drugs useful for selecting for the presence of a selectable marker include, for example, G418 for Neo, hygromycin for Hyg, histidinol for hisD, xanthine for Gpt, and bleomycin for Ble (see Ausubel et al, supra, (1999); U.S. Pat. No. 5,981,830). DNA constructs of the invention can incorporate a positive selectable marker, a negative selectable marker, or both (see, for example, U.S. Pat. No. 5,981,830).

Various mammalian cell culture systems can also be employed to express a recombinant protein. Examples of mammalian expression systems include the COS-7 lines of monkey kidney fibroblasts, described by Gluzman, Cell, 23: 175 (1981). Other cell lines capable of expressing a compatible vector include, for example, the C127, 3T3, CHO, HeLa and BHK cell lines. Mammalian expression vectors will generally comprise an origin of replication, a suitable promoter and enhancer, and also any necessary ribosome binding sites, polyadenylation site, splice donor and acceptor sites, transcriptional termination sequences, and 5' flanking nontranscribed sequences. DNA sequences derived from the SV40 splice, and polyadenylation sites may be used to provide required nontranscribed genetic elements.

The polypeptides can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Recovery can be facilitated if the polypeptide is expressed at the surface of the cells, but such is not a prerequisite. Recovery may also be desirable of cleavage products that are cleaved following expression of a longer form of the polypeptide. Protein refolding steps as known in this art can be used, as necessary, to complete configuration of the mature protein. High performance liquid chromatography (HPLC) can be employed for final purification steps.

Human constant region DNA sequences can be isolated in accordance with well-known procedures from a variety of human cells.

The present invention pertains in particular to antibodies which are characterized in that they bind to Aβ N3pE peptides with a high affinity. The present invention also pertains to antibodies which are characterized in that they bind to Aβ N3pE peptides or immunologically active fragments thereof with a high affinity. Said high affinity means in the context of the present invention an affinity of a $K_D$ value of $10^{-5}$ M, $10^{-6}$ M or $10^{-7}$ M or better, preferably a $K_D$ value of $10^{-8}$ M or better, and even more preferably a $K_D$ value of $10^{-9}$ M-$10^{-12}$ M. Thereby, the inventive antibodies bind to monomeric Aβ N3pE with a higher affinity than previously known antibodies.

Preferably, the binding epitope of the antibodies of the present invention in Aβ N3pE binds is an epitope, which carries a pyroglutamate at the N-terminus. More preferably, the binding epitope of the antibody of the invention is selected from the group consisting of

| | |
|---|---|
| pEFRHDSGYEVHHQKLV, | (SEQ ID NO: 23) |
| pEFRHDSGYEVHHQKL, | (SEQ ID NO: 24) |
| pEFRHDSGYEVHHQK, | (SEQ ID NO: 25) |
| pEFRHDSGYEVHHQ, | (SEQ ID NO: 26) |
| pEFRHDSGYEVHH, | (SEQ ID NO: 27) |
| pEFRHDSGYEVH, | (SEQ ID NO: 28) |
| pEFRHDSGYEV, | (SEQ ID NO: 29) |
| pEFRHDSGYE, | (SEQ ID NO: 30) |
| pEFRHDSGY, | (SEQ ID NO: 31) |
| pEFRHDSG, | (SEQ ID NO: 32) |
| pEFRHDS, | (SEQ ID NO: 33) |
| pEFRHD | (SEQ ID NO: 34) |
| pEFRH, and | (SEQ ID NO: 35) |
| pEFR. | (SEQ ID NO: 36) |

Most preferably, the antibodies of the invention do not bind to binding epitopes that do not carry a pyroglutamate at the N-terminus.

Even most preferably, when binding to the aforementioned and subsequently mentioned binding epitopes, the antibodies of the invention always bind to sequences or parts of sequences, which contain the pyroglutamate at the N-terminus. The antibodies of the invention do not bind to sequences or parts of sequences, which do not contain the pyroglutamate at the N-terminus.

Further, the antibody of the invention can also bind to an Aβ N3pE variant.

In the context of the present invention, an Aβ N3pE variant is in particular pE-Aβ$_{3-38}$,
pE-Aβ$_{3-40}$,
pE-Aβ$_{3-42}$ Further variants of Aβ N3pE peptides are all Aβ N3pE variants, which have been shown to accumulate in the brain as a consequence of Alzheimer's disease or preceding Alzheimer's disease. These are the pE-Aβ$_{3-X}$ peptides, wherein x is defined as an integer between 19 and 42, e.g. in the above pE-Aβ$_{3-42}$, "42" would be the integer for "x".

In the context of the present invention a "functional variant" of the inventive antibody is an antibody which retains the binding capacities, in particular binding capacities with high affinity to a pE-Aβ$_{3-X}$ peptide. The provision of such functional variants is known in the art and encompasses the above-mentioned possibilities, which were indicated under the definition of antibodies and fragments thereof.

In a further embodiment, the antibody is an antibody fragment, as defined above.

In a further preferred embodiment, the antibody of the invention is a humanized and de-immunized antibody which has the complementarity-determining regions (CDRs) of the above-defined antibodies. Preferably, the antibody can be labeled; possible labels are those as mentioned above and all those known to a person skilled in the art of diagnostic uses of antibodies in particular.

In another embodiment, the antibodies may be immobilized on a solid phase.

In another embodiment, the antibodies according to the invention and as described herein before or a fragments thereof, exhibit a binding affinity to an Aβ N3pE oligomer, fiber, fibril or filament which is at least 2 times, particularly at least 4 times, particularly at least 10 times, particularly at least 15 times, more particularly at least 20 times, but especially at least 25 times higher than the binding affinity to an Aβ N3pE monomer.

In still another embodiment, antibodies or fragments thereof are provided as described herein before, which substantially bind to aggregated Aβ, including Aβ plaques, which contain Aβ N3pE, in the mammalian, particularly the human brain but, preferably, do not show any significant cross-reactivity with amyloid precursor protein (APP).

In another aspect of the invention, antibodies or fragments thereof are provided as described herein before, which antibodies substantially bind to oligomeric or polymeric amyloid, which contains Aβ N3pE, particularly amyloid β (AR) in the mammalian, particularly the human brain but, preferably, do not show any significant cross-reactivity with amyloid precursor protein (APP).

The present invention relates also to compositions comprising said antibodies and the use of said compositions for the treatment of amyloidosis, especially for the treatment of neurodegenerative disease in a mammal, in particular in a human. Said neurodegenerative disease is in particular selected from the group consisting of mild cognitive impairment (MCI), Alzheimer's disease (AD), like for instance sporadic Alzheimer's disease (SAD) or Familial Alzheimer's dementias (FAD) like Familial British Dementia (FBD) and Familial Danish Dementia (FDD), neurodegeneration in Down Syndrome. Preferably, said neurodegenerative disease is Alzheimer's disease.

Thus, in a preferred embodiment, the present invention is directed to a method of treating and/or preventing conditions characterized by the formation of plaques comprising Aβ N3pE in mammals, preferably in humans, which method comprises administering, preferably peripherally, to a human in need of such treatment a therapeutically or prophylactically effective amount of an monoclonal antibody of the invention or a immunologically reactive fragment thereof, which antibody specifically binds to an epitope of the Aβ N3pE peptide that carries pyroglutamate at the N-terminus.

In another embodiment, the invention is directed to a method to inhibit the formation of amyloid plaques and to clear or remove amyloid plaques in mammals, preferably in humans, which method comprises administering to a human subject in need of such inhibition an effective amount of an antibody that binds to Aβ N3pE in the circulation, body fluids or tissues, especially in the brain and further preferably, leads to the clearance of Aβ N3pE in plasma and the brain.

Accordingly, the invention also provides methods of reversing cognitive decline, improving cognition, treating cognitive decline, and preventing cognitive decline in a subject diagnosed with mild cognitive impairment (MCI), Alzheimer's disease (AD), like for instance sporadic Alzheimer's disease (SAD) or Familial Alzheimer's dementias (FAD) like Familial British Dementia (FBD) and Familial Danish Dementia (FDD), neurodegeneration in Down Syndrome and clinical or pre-clinical cerebral amyloid angiopathy, preferably Alzheimer's disease comprising administering to the subject an effective amount of an antibody of the invention.

The invention also provides the use of an antibody of the invention for the manufacture of a medicament, for treating, preventing, or reversing mild cognitive impairment (MCI), Alzheimer's disease (AD), like for instance sporadic Alzheimer's disease (SAD) or Familial Alzheimer's dementias (FAD) like Familial British Dementia (FBD) and Familial Danish Dementia (FDD), neurodegeneration in Down Syndrome and clinical or pre-clinical cerebral amyloid angiopathy, preferably Alzheimer's disease; or to reverse cognitive decline, improve cognition, treat cognitive decline, and prevent cognitive decline in a subject diagnosed with mild cognitive impairment (MCI), Alzheimer's disease (AD), like for instance sporadic Alzheimer's disease (SAD) or Familial Alzheimer's dementias (FAD) like Familial British Dementia (FBD) and Familial Danish Dementia (FDD), neurodegeneration in Down Syndrome and clinical or pre-clinical cerebral amyloid angiopathy, preferably Alzheimer's disease.

The invention further provides the antibodies disclosed herein for use in the prevention, treatment, or the reversion of mild cognitive impairment (MCI), Alzheimer's disease (AD), like for instance sporadic Alzheimer's disease (SAD) or Familial Alzheimer's dementias (FAD) like Familial British Dementia (FBD) and Familial Danish Dementia (FDD), neurodegeneration in Down Syndrome and clinical or pre-clinical cerebral amyloid angiopathy, preferably Alzheimer's disease; for treating, preventing, or the reversion of cognitive decline, improvement of cognition, treatment of cognitive decline, and prevention of cognitive decline in a subject diagnosed with mild cognitive impairment (MCI), Alzheimer's disease (AD), like for instance sporadic Alzheimer's disease (SAD) or Familial Alzheimer's dementias (FAD) like Familial British Dementia (FBD) and Familial Danish Dementia (FDD), neurodegeneration in Down Syndrome and clinical or pre-clinical cerebral amyloid angiopathy, preferably Alzheimer's disease; or the inhibition of the formation of anyloid plaques or the effects of Aβ N3pE in mammals, preferably in humans.

In a specific embodiment the invention provides a method for retaining or increasing cognitive memory capacity but, particularly, for restoring the cognitive memory capacity of a mammal, particularly a human, suffering from memory impairment by administering to an animal, particularly a mammal or a human, an antibody of the invention, or a pharmaceutical composition comprising an antibody according to the invention and as described herein before.

The invention further provides methods to assess the response of a human subject to treatment with an antibody that binds Aβ N3pE or a variant thereof, comprising:
a) administering an antibody of the invention or a fragment thereof to the subject; and
b) measuring the concentration of Aβ N3pE in a biological sample taken from the subject.

The invention also provides a method of treating a human subject with an antibody that binds Aβ N3pE or a variant thereof, comprising:
a) administering a first amount of the antibody or fragment thereof to the subject;
b) within 3 hours to two weeks after administering the first dose, measuring the concentration of Aβ N3pE in a biological sample taken from the subject;
c) if necessary, calculating a second amount of antibody or fragment thereof based on the result of step b), which second amount is the same as or different than the first amount; and
d) administering the second amount of the antibody or fragment.

The invention also includes a method of assessing in a mammalian, preferably a human subject the efficacy of an antibody that binds to Aβ N3pE, or a fragment thereof, for inhibiting or preventing Aβ N3pE related amyloid plaque formation, for reducing the load of Aβ N3pE containing plaques, for reducing the effects of toxic Aβ N3pE and variants thereof, or for treating a condition or a disease associated with plaques containing Aβ N3pE, comprising:
   a) obtaining a first biological sample form the subject;
   b) measuring a baseline concentration of Aβ N3pE in the first sample;
   c) administering an antibody of the invention or fragment thereof to the subject;
   d) within 3 hours to two weeks after administering the antibody or fragment thereof, obtaining a second biological sample from the subject; and
   e) measuring the concentration of Aβ N3pE in the second biological sample; wherein, efficacy is related to the quantity of Aβ N3pE bound to the antibody in the blood and the concentration of Aβ N3pE, in particular the reduction of the concentration thereof, in the second biological sample compared to the first biological sample.

The biological sample may be any sample, for example from a human. In one specific example, the sample is a tissue sample, a body fluid sample or a cell sample. In one embodiment, the biological sample is selected from the group consisting of blood, serum, urine, cerebrospinal fluid (CSF), plasma, lymph, saliva, sweat, pleural fluid, synovial fluid, tear fluid, bile and pancreas secretion. In a further embodiment, the biological sample is plasma. In a preferred embodiment, the biological sample is CSF.

The biological sample can be obtained from a subject in a manner well-known to a person skilled in the art. In particular, a blood sample can be obtained from a subject and the blood sample can be separated into serum and plasma by conventional methods. The subject, from which the biological sample is obtained is preferably a subject suspected of being afflicted with a disease or condition of amyloidosis, preferably Alzheimer's disease, at risk of developing Alzheimer's disease and/or being at risk of or having any other kind of dementia. In particular, the sample is obtained from a subject suspected of having Mild Cognitive Impairment (MCI) and/or being in the early stages of Alzheimer's disease.

The efficacy of the antibodies of the invention in the diagnosis, prevention and/or treatment of amyloidosis, such as mild cognitive impairment, Alzheimer's Disease, Familial British Dementia or Familial Danish Dementia and, e.g. neurodegeneration in Down Syndrome can be tested in existing animal models of Alzheimer's disease.

Suitable animal models of Alzheimer's Disease are reviewed in McGowan et al. TRENDS in Genetics, Vol. 22, No. May 2006, pp 281-289, and are selected from PDAPP, Tg2576, APP23, TgCRND8, $PSEN1_{M146V}$ or $PSEN1_{M146L}$, PSAPP, $APP_{Dutch}$, BRI-Aβ40 and BRI-Aβ42, JNPL3, $Tau_{P301S}$, $Tau_{V337M}$, $Tau_{R406W}$, rTg4510, $H_{tau}$, TAPP, 3xTgAD, as described below.

PDAPP: First mutant APP transgenic model with robust plaque pathology. Mice express a human APP cDNA with the Indiana mutation ($APP_{V717F}$). Plaque pathology begins between 6-9 months in hemizygous PDAPP mice. There is synapse loss but no overt cell loss and not NFT pathology is observed. This model has been used widely in vaccination therapy strategies.

Tg2576: Mice express mutant $APP_{SWE}$ under control of the hamster prion promoter. Plaque pathology is observed from 9 months of age.

These mice have cognitive deficits but no cell loss or NFT pathology. This model is one of the most widely used transgenic models in the field of Alzheimer's disease.

APP23: Mice express mutant $APP_{SWE}$ under control of the Thy1 promoter. Prominent cerebrovascular amyloid, amyloid deposits are observed from 6 months of age and some hippocampal neuronal loss is associated with amyloid plaque formation.

TgCRND8: Mice express multiple APP mutations (Swedish plus Indiana). Cognitive deficits coincide with rapid extracellular plaque development at ~3 months of age. The cognitive deficits can be reversed by Aβ vaccination therapy.

$PSEN1_{M146V}$ or $PSEN1_{M146L}$ (lines 6.2 and 8.9, respectively) These models where the first demonstration in vivo that mutant PSEN1 selectively elevates A842. No overt plaque pathology is observed.

PSAPP (Tg2576x$PSEN1_{M146L}$, PSEN1-A246E+ $APP_{SWE}$): Bigenic transgenic mice, with the addition of the mutant PSEN1 transgene which markedly accelerated amyloid pathology compared with singly transgenic mutant APP mice, demonstrating that the PSEN1-driven elevation of Aβ 42 enhances plaque pathology.

$APP_{Dutch}$: Mice express APP with the Dutch mutation that causes hereditary cerebral hemorrhage with amyloidosis-Dutch type in humans. $APP_{Dutch}$ mice develop severe congophilic amyloid angiopathy. The addition of a mutant PSEN1 transgene redistributes the amyloid pathology to the parenchyma indicating differing roles for Aβ40 and Aβ42 in vascular and parenchymal amyloid pathology.

BRI-Aβ40 and BRI-Aβ42: Mice express individual A isoforms without APP over-expression. Only mice expressing Aβ42 develop senile plaques and CAA, whereas BRI-Aβ40 mice do not develop plaques, suggesting that Aβ42 is essential for plaque formation.

JNPL3: Mice express 4R0N MAPT with the P301L mutation. This is the first transgenic model, with marked tangle pathology and cell loss, demonstrating that MAPT alone can cause cellular damage and loss. JNPL3 mice develop motor impairments with age owing to servere pathology and motor neutron loss in the spinal cord.

$Tau_{P301S}$: Tansgenic mice expressing the shortest isoform of 4R MAPT with the P301S mutation. Homozygous mice develop severe paraparesis at 5-6 months of age with widespread neurofibrillary pathology in the brain and spinal cord and neuronal loss in the spinal cord.

$Tau_{V337M}$: Low level synthesis of 4R MAPT with the V337M mutation (1/10 endogenous MAPT) driven by the promoter of platelet-derived growth factor (PDGF). The development of neurofibrillary pathology in these mice suggests the nature of the MAPT rather than absolute MAPT intracellular concentration drives pathology.

$Tau_{R406W}$: Mice expressing 4R human MAPT with the R406W mutation under control of the CAMKII promoter. Mice develop MAPT inclusions in the forebrain from 18 months of age and have impaired associative memory.

rTg4510: Inducible MAPT transgenic mice using the TET-off system. Abnormal MAPT pathology occurs from one month of age. Mice have progressive NFT pathology and severe cell loss. Cognitive deficits are evident from 2.5 months of age. Turning off the transgene improves cognitive performance but NT pathology worsens.

$H_{tau}$: Transgenic mice expressing human genomic MAPT only (mouse MAPT knocked-out). Htau mice accumulate hyperphosphorylated MAPT from 6 months and develop Thio-S-positive NFT by the time they are 15 months old.

TAPP (Tg2576xJNPL3): Increased MAPT forebrain pathology in TAPP mice compared with JNPL3 suggesting mutant APP and/or A can affect downstream MAPT pathology.

3xTgAD: Triple transgenic model expressing mutant $APP_{SWE}$, $MAPT_{P301L}$ on a $PSEN1_{M146V}$ 'knock-in' background (PSNE1-KI). Mice develop plaques from 6 months and MAPT pathology from the time they are 12 months old, strengthening the hypothesis that APP or Aβ can directly influence neurofibrillary pathology.

Moreover, WO 2009/034158 discloses non-human transgenic animal models, wherein the transgene encodes at least one amyloid beta (Aβ) peptide selected from the group consisting of AβN3E-42, AβN3Q-42, AβN3E-40 and AβN3Q-40. These Aβ peptides are substrates of QC and QPCTL, resulting in the cyclization of the N-terminal glutamine (Q) or glutamate (N) to pyroglutamate (pGlu). Thus, these transgenic animal models provide a model system for the investigation of the effect of pGlu-Aβ peptides on the course of the development of neurodegenration.

Anti-Aβ pN3pE antibodies may also be useful in diagnostic assays for Aβ pN3pE, e.g. detecting its occurrence in specific cells, tissues, or serum. Thus, the antibodies according to the present invention are especially useful in a diagnostic method to detect amyloidosis, in particular a neurodegenerative disease selected from the group consisting of mild cognitive impairment (MCI), Alzheimer's disease (AD), like for instance sporadic Alzheimer's disease (SAD) or Familial Alzheimer's dementias (FAD) like Familial British Dementia (FBD) and Familial Danish Dementia (FDD), neurodegeneration in Down Syndrome; preferably Alzheimer's disease.

For diagnostic applications, the antibody typically will be labelled with a detectable moiety. Numerous labels are available which can be generally grouped into the following categories:

(a) Radioisotopes, such as $^{35}S$, $^{14}C$, $^{125}I$, $^{3}H$, and $^{131}I$. The antibody can be labeled with the radioisotope using the techniques described in Current Protocols in Immunology, Volumes 1 and 2, Gutigen et al., Ed., Wiley-Interscience. New York, New York Pubs., (1991) for example and radioactivity can be measured using scintillation counting.

(b) Fluorescent labels such as rare earth chelates (europium chelates) or fluorescein and its derivatives, rhodamine and its derivatives, dansyl, Lissamine, phycoerythrin and Texas Red are available. The fluorescent labels can be conjugated to the antibody using the techniques disclosed in Current Protocols in Immunology, supra for example. Fluorescence can be quantified using a fluorimeter.

(c) Various enzyme-substrate labels are available. The enzyme generally catalyses a chemical alteration of the chromogenic substrate which can be measured using various techniques. For example, the enzyme may catalyze a color change in a substrate, which can be measured spectrophotometrically. Alternatively, the enzyme may alter the fluorescence or chemiluminescence of the substrate. Techniques for quantifying a change in fluorescence are described above. The chemiluminescent substrate becomes electronically excited by a chemical reaction and may then emit light which can be measured (using a chemiluminometer, for example) or donates energy to a fluorescent acceptor. Examples of enzymatic labels include luciferases (e.g, firefly luciferase and bacterial luciferase; U.S. Pat. No. 4,737,456), luciferin, 2,3-dihydrophthalazinediones, malate dehydrogenase, urease, peroxidase such as horseradish peroxidase (HRPO), alkaline phosphatase. 0-galactosidase, glucoamylase, lysozyme, saccharide oxidases (e.g., glucose oxidase, galactose oxidase, and glucose-6-phosphate dehydrogenase), heterocyclic oxidases (such as uricase and xanthine oxidase), lactoperoxidase, microperoxidase, and the like. Techniques for conjugating enzymes to antibodies are described in O'Sullivan et al., Methods for the Preparation of Enzyme-Antibody Conjugates for use in Enzyme Immunoassay, in Methods in Enzym (ed Langone & H. Van Vunakis), Academic Press, New York, 73: 147-166 (1981).

Examples of enzyme-substrate combinations include, for example:

(i) Horseradish peroxidase (HRPO) with hydrogen peroxidase as a substrate, wherein the hydrogen peroxidase oxidizes a dye precursor (e.g. orthophenylene diamine (OPD) or 3,3',5,5'-tetramethyl benzidine hydrochloride (TMB));

(ii) alkaline phosphatase (AP) with para-Nitrophenyl phosphate as chromogenic substrate; and (iii) R-D-galactosidase (R-D-Gal) with a chromogenic substrate (e.g. p-nitrophenyl-R-D-galactosidase) or the fluorogenic substrate 4-methylumbelliferyl-R-D-galactosidase.

Numerous other enzyme-substrate combinations are available to those skilled in the art.

Sometimes, the label is indirectly conjugated with the antibody. The skilled artisan will be aware of various techniques for achieving this. For example, the antibody can be conjugated with biotin and any of the three broad categories of labels mentioned above can be conjugated with avidin, or vice versa. Biotin binds selectively to avidin and thus, the label can be conjugated with the antibody in this indirect manner. Alternatively, to achieve indirect conjugation of the label with the antibody, the antibody is conjugated with a small hapten (e.g. digoxin) and one of the different types of labels mentioned above is conjugated with an anti-hapten antibody (e.g. anti-digoxin antibody). Thus, indirect conjugation of the label with the antibody can be achieved.

The antibodies of the present invention may be employed in any known assay method, such as competitive binding assays, direct and indirect sandwich assays, and immunoprecipitation assays. Zola, Monoclonal Antibodies A Manual of Techniques, pp. 147-158 (CRC Press. Inc., 1987)

Competitive binding assays rely on the ability of a labeled standard to compete with the test sample analyte for binding with a limited amount of antibody. The amount of Aβ N3pE in the test sample is inversely proportional to the amount of standard that becomes bound to the antibodies. To facilitate determining the amount of standard that becomes bound, the antibodies generally are insolubilized before or after the competition, so that the standard and analyte that are bound to the antibodies may conveniently be separated from the standard and analyte which remain unbound.

Sandwich assays involve the use of two antibodies, each capable of binding to a different immunogenic portion, or epitope, of the protein to be detected. In a sandwich assay, the test sample analyte is bound by a first antibody which is immobilized on a solid support, and thereafter a second antibody binds to the analyte, thus forming an insoluble three-part complex. The second antibody may itself be labeled with a detectable moiety (direct sandwich assays) or may be measured using an anti-immunoglobulin antibody that is labeled with a detectable moiety (indirect sandwich assay). For example, one preferable type of sandwich assay is an ELISA assay, in which case the detectable moiety is an enzyme.

For immunohistochemistry, the tissue sample may be fresh or frozen or may be embedded in paraffin and fixed with a preservative such as formalin, for example.

The present invention also relates to a composition which comprises the antibodies as defined above, wherein said composition is a composition for a diagnostic use, especially for the diagnosis of a neurodegenerative disease selected from the group consisting of mild cognitive impairment (MCI), Alzheimer's disease (AD), like for instance sporadic Alzheimer's disease (SAD) or Familial Alzheimer's dementias (FAD) like Familial British Dementia (FBD) and Familial Danish Dementia (FDD), neurodegeneration in Down Syndrome; preferably Alzheimer's disease; in particular by detection of Aβ N3pE or variants thereof in a biological sample.

Diagnostic Kits

As a matter of convenience, the antibody of the present invention can be provided in a kit, i.e., a packaged combination of reagents in predetermined amounts with instructions for performing the diagnostic assay. Where the antibody is labelled with an enzyme, the kit will include substrates and cofactors required by the enzyme (e.g. a substrate precursor which provides the detectable chromophore or fluorophore). In addition, other additives may be included such as stabilizers, buffers (e.g. a block buffer or lysis buffer) and the like. The relative amounts of the various reagents may be varied widely to provide for concentrations in solution of the reagents which substantially optimize the sensitivity of the assay. Particularly, the reagents may be provided as dry powders, usually lyophilized, including excipients which on dissolution will provide a reagent solution having the appropriate concentration.

The diagnostic kit according to the invention may contain a further biologically active substance as described below. Especially preferred for the use in the diagnostic kit as said further further biologically active substance is an inhibitor of glutaminyl cyclase.

The diagnostic kit of the invention is especially useful for the detection and diagnosis of amyloid-associated diseases and conditions, in particular neurodegenerative diseases selected from the group consisting of mild cognitive impairment (MCI), Alzheimer's disease (AD), like for instance sporadic Alzheimer's disease (SAD) or Familial Alzheimer's dementias (FAD) like Familial British Dementia (FBD) and Familial Danish Dementia (FDD), neurodegeneration in Down Syndrome; preferably Alzheimer's disease.

The present invention also pertains to the antibody of the invention or the composition comprising the antibody, both as defined above, for use in an in vitro diagnostic method. In particular, this diagnostic method is directed to diagnosis of a neurodegenerative disease selected from the group consisting of mild cognitive impairment (MCI), Alzheimer's disease (AD), like for instance sporadic Alzheimer's disease (SAD) or Familial Alzheimer's dementias (FAD) like Familial British Dementia (FBD) and Familial Danish Dementia (FDD), neurodegeneration in Down Syndrome; preferably Alzheimer's disease; especially by detecting an Aβ N3pE or variants thereof in a biological sample.

In a particularly preferred embodiment, the present invention pertains to the following method:

In vitro or in situ diagnostic method for the diagnosis of an amyloid-associated disease or condition, preferably Alzheimer's disease, comprising the following steps:
contacting an antibody according to the invention with a sample, preferably selected from a serum, liquor or CSF sample, most preferably a serum sample; or a specific body part or body area of a subject suspected to be afflicted with said condition or disease, and
detecting binding of the antibody to Aβ N3pE, from the sample.

More particularly, the invention relates to a method of diagnosis of an amyloid-associated disease or condition, preferably Alzheimer's disease, comprising detecting the immunospecific binding of an antibody of the invention or an immunologically active fragment thereof to Aβ N3pE, in a sample or in situ which includes the steps of
(a) bringing the sample or a specific body part or body area suspected to contain the amyloid protein into contact with an antibody of the invention, or a fragment thereof;
(b) allowing the antibody and/or a functional part thereof, to bind to Aβ N3pE to form an immunological complex;
(c) detecting the formation of the immunological complex; and
(d) correlating the presence or absence of the immunological complex with the presence or absence of Aβ N3pE in the sample or specific body part or area.

Also comprised is a method of determining the extent of amyloidogenic plaque burden in a tissue and/or body fluids comprising (a) obtaining a sample representative of the tissue and/or body fluids under investigation;
(b) testing said sample for the presence of amyloid protein with an antibody according to the invention, or a chimeric antibody or a fragment thereof;
(c) determining the amount of antibody bound to the protein; and
(d) calculating the plaque burden in the tissue and/or body fluids.

In particular, the invention relates to a method of determining the extent of amyloidogenic plaque burden in a tissue and/or body fluids, wherein the formation of the immunological complex in step c) is determined such that presence or absence of the immunological complex correlates with presence or absence of amyloid protein, in particular Aβ N3pE.

In still another embodiment, the invention relates to a composition comprising the antibody according to the invention, or a chimeric antibody or a fragment thereof, and as described herein before including any functionally equivalent antibody or any derivative or functional parts thereof, in particular a composition which is a pharmaceutical composition optionally further comprising a pharmaceutically acceptable carrier.

In another embodiment of the invention, said composition comprises the antibody of the invention in a therapeutically effective amount.

Further comprised by the invention is a mixture comprising an antibody of the invention, or a chimeric antibody or a fragment thereof, and as described herein before including any functionally equivalent antibody or any derivative or functional parts thereof, in a therapeutically effective amount and, optionally, a further biologically active substance and/or a pharmaceutically acceptable carrier and/or a diluent and/or an excipient.

In particular, the invention relates to a mixture, wherein the further biologically active substance is a compound used in the medication of amyloidosis, a group of diseases and disorders associated with amyloid or amyloid-like protein such as Aβ N3pE involved in neurodegenerative diseases selected from the group consisting of mild cognitive impairment (MCI), Alzheimer's disease (AD), like for instance sporadic Alzheimer's disease (SAD) or Familial Alzheimer's dementias (FAD) like Familial British Dementia (FBD) and Familial Danish Dementia (FDD), neurodegeneration in Down Syndrome; preferably Alzheimer's disease.

In another embodiment of the invention, the other biologically active substance or compound may also be a therapeutic agent that may be used in the treatment of amyloidosis caused by Aβ N3pE or may be used in the medication of other neurological disorders.

The other biologically active substance or compound may exert its biological effect by the same or a similar mechanism as the antibody according to the invention or by an unrelated mechanism of action or by a multiplicity of related and/or unrelated mechanisms of action.

Generally, the other biologically active compound may include neutron-transmission enhancers, psychotherapeutic drugs, acetylcholine esterase inhibitors, calcium-channel blockers, biogenic amines, benzodiazepine tranquillizers, acetylcholine synthesis, storage or release enhancers, acetylcholine postsynaptic receptor agonists, monoamine oxidase-A or -B inhibitors, N-methyl-D-aspartate glutamate receptor antagonists, non-steroidal anti-inflammatory drugs, antioxidants, and serotonergic receptor antagonists.

More particularly, the invention relates to a mixture comprising at least one compound selected from the group consisting of compounds effective against oxidative stress, anti-apoptotic compounds, metal chelators, inhibitors of DNA repair such as pirenzepin and metabolites, 3-amino-1-propanesulfonic acid (3 APS), 1,3-propanedisulfonate (1,3PDS), α-secretase activators, β- and γ-secretase inhibitors, tau proteins, neurotransmitter, /3-sheet breakers, attractants for amyloid beta clearing/depleting cellular components, inhibitors of N-terminal truncated amyloid beta including pyroglutamated amyloid beta 3-42, such as inhibitors of glutaminyl cyclase, anti-inflammatory molecules, or cholinesterase inhibitors (ChEIs) such as tacrine, rivastigmine, donepezil, and/or galantamine, M1 agonists and other drugs including any amyloid or tau modifying drug and nutritive supplements, and nutritive supplements, together with an antibody according to the present invention and, optionally, a pharmaceutically acceptable carrier and/or a diluent and/or an excipient.

The invention further relates to a mixture, wherein the compound is a cholinesterase inhibitor (ChEIs), particularly a mixture, wherein the compound is one selected from the group consisting of tacrine, rivastigmine, donepezil, galantamine, niacin and memantine.

In a further embodiment, the mixtures according to the invention may comprise niacin or memantine together with an antibody according to the present invention and, optionally, a pharmaceutically acceptable carrier and/or a diluent and/or an excipient.

In a further embodiment, the mixtures according to the invention may comprise a glutaminyl cyclase inhibitor together with an antibody according to the present invention and, optionally, a pharmaceutically acceptable carrier and/or a diluent and/or an excipient.

Preferred inhibitors of glutaminyl cyclase are described in WO 2005/075436, WO 2008/055945, WO 2008/055947, WO 2008/055950, WO 2008/065141, WO 2008/110523, WO 2008/128981, WO 2008/128982, WO 2008/128983, WO 2008/128984, WO 2008/128985, WO 2008/128986, WO 2008/128987, WO 2010/026212, WO 2011/131748, WO 2011/029920, WO 2011/107530, WO 2011/110613, WO 2012/123563 and WO 2014/140279, the disclosure of which is incorporated herein by reference.

In still another embodiment of the invention mixtures are provided that comprise "atypical antipsychotics" such as, for example clozapine, ziprasidone, risperidone, aripiprazole or olanzapine for the treatment of positive and negative psychotic symptoms including hallucinations, delusions, thought disorders (manifested by marked incoherence, derailment, tangentiality), and bizarre or disorganized behavior, as well as anhedonia, flattened affect, apathy, and social withdrawal, together with an antibody, particularly a monoclonal antibody according to the invention, but particularly a chimeric antibody or a fragment thereof, or an antibody or a fragment thereof according to the invention and as described herein and, optionally, a pharmaceutically acceptable carrier and/or a diluent and/or an excipient.

In a specific embodiment of the invention, the compositions and mixtures according to the invention and as described herein before comprise the antibody of the invention and the biologically active substance, respectively, in a therapeutically effective amount.

Other compounds that can be suitably used in mixtures in combination with the antibody according to the present invention are described in WO2008/065141 (see especially pages 37/38), including PEP-inhibitors (pp. 43/44), LiCl, inhibitors of dipeptidyl aminopeptidases, preferably inhibitors of DP IV or DP IV-like enzymes (see pp. 48/49); acetylcholinesterase (ACE) inhibitors (see p. 47), PIMT enhancers, inhibitors of beta secretases (see p. 41), inhibitors of gamma secretases (see pp. 41/42), inhibitors of neutral endopeptidase, inhibitors of phosphodiesterase-4 (PDE-4) (see pp. 42/43), TNFalpha inhibitors, muscarinic M1 receptor antagonists (see p. 46), NMDA receptor antagonists (see pp. 47/48), sigma-1 receptor inhibitors, histamine H3 antagonists (se p. 43), immunomodulatory agents, immunosuppressive agents or an agent selected from the group consisting of antegren (natalizumab), Neurelan (fampridine-SR), campath (alemtuzumab), IR 208, NBI 5788/MSP 771 (tiplimotide), paclitaxel, Anergix.MS (AG 284), SH636, Differin (CD 271, adapalene), BAY 361677 (interleukin-4), matrix-metalloproteinase-inhibitors (e.g. BB 76163), interferon-tau (trophoblastin) and SAIK-MS; beta-amyloid antibodies (see p. 44), cysteine protease inhibitors (see p. 44); MCP-1 antagonists (see pp. 44/45), amyloid protein deposition inhibitors (see 42) and beta amyloid synthesis inhibitors (see p. 42), which document is incorporated herein by reference.

In another embodiment, the invention relates to a mixture comprising the antibody according to the invention, or a chimeric antibody or a fragment thereof and as described herein before and/or the biologically active substance in a therapeutically effective amount.

The pharmaceutical compositions may be formulated with pharmaceutically acceptable carriers or diluents as well as any other known adjuvants and excipients in accordance with conventional techniques such as those disclosed in Remington: The Science and Practice of Pharmacy, 21th Edition, Gennaro, Ed., Mack Publishing Co., Easton, PA, 2005.

The pharmaceutically acceptable carriers or diluents as well as any other known adjuvants and excipients should be suitable for the chosen antibody of the present invention and the chosen mode of administration. Suitability for carriers and other components of pharmaceutical compositions is determined based on the lack of significant negative impact on the desired biological properties of the chosen antibody or pharmaceutical composition of the present invention (e.g., less than a substantial impact (10% or less relative inhibition, 5% or less relative inhibition, etc.)) on antigen binding.

A pharmaceutical composition of the present invention may also include diluents, fillers, salts, buffers, detergents (e.g., a nonionic detergent, such as Tween-20 or Tween-80), stabilizers (e.g., sugars or protein-free amino acids), preservatives, tissue fixatives, solubilizers, and/or other materials suitable for inclusion in a pharmaceutical composition.

The actual dosage levels of the active ingredients in the pharmaceutical compositions of the present invention may be varied so as to obtain an amount of the active ingredient which is effective to achieve the desired therapeutic response for a particular patient, composition, and mode of administration. The selected dosage level will depend upon a variety of pharmacokinetic factors including the activity of the particular compositions of the present invention employed, or the amide thereof, the route of administration, the time of administration, the rate of excretion of the particular antibody being employed, the duration of the treatment, other drugs, compounds and/or materials used in combination with the particular compositions employed, the age, sex, weight, condition, general health and prior medical history of the patient being treated, and like factors well known in the medical arts.

The pharmaceutical composition may be administered by any suitable route and mode. Suitable routes of administering an antibody of the present invention in vivo and in vitro are well known in the art and may be selected by those of ordinary skill in the art.

In one embodiment, a pharmaceutical composition of the present invention is administered parenterally.

The phrases "parenteral administration" and "administered parenterally" as used herein means modes of administration other than enteral and topical administration, usually by injection, and include epidermal, intravenous, intramuscular, intraarterial, intrathecal, intracapsular, intraorbital, intracardiac, intradermal, intraperitoneal, intratendinous, transtracheal, subcutaneous, subcuticular, intraarticular, subcapsular, subarachnoid, intraspinal, intracranial, intrathoracic, epidural and intrasternal injection and infusion.

In one embodiment that pharmaceutical composition is administered by intravenous or subcutaneous injection or infusion.

Pharmaceutically acceptable carriers include any and all suitable solvents, dispersion media, coatings, antibacterial and antifungal agents, isotonicity agents, antioxidants and absorption delaying agents, and the like that are physiologically compatible with an antibody of the present invention.

Examples of suitable aqueous and nonaqueous carriers which may be employed in the pharmaceutical compositions of the present invention include water, saline, phosphate buffered saline, ethanol, dextrose, polyols (such as glycerol, propylene glycol, polyethylene glycol, and the like), and suitable mixtures thereof, vegetable oils, such as olive oil, corn oil, peanut oil, cottonseed oil, and sesame oil, carboxymethyl cellulose colloidal solutions, tragacanth gum and injectable organic esters, such as ethyl oleate, and/or various buffers. Other carriers are well known in the pharmaceutical arts.

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active antibody, use thereof in the pharmaceutical compositions of the present invention is contemplated.

Proper fluidity may be maintained, for example, by the use of coating materials, such as lecithin, by the maintenance of the required particle size in the case of dispersions, and by the use of surfactants.

Pharmaceutical compositions of the present invention may also comprise pharmaceutically acceptable antioxidants for instance (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Pharmaceutical compositions of the present invention may also comprise isotonicity agents, such as sugars, polyalcohols, such as mannitol, sorbitol, glycerol or sodium chloride in the compositions.

The pharmaceutical compositions of the present invention may also contain one or more adjuvants appropriate for the chosen route of administration such as preservatives, wetting agents, emulsifying agents, dispersing agents, preservatives or buffers, which may enhance the shelf life or effectiveness of the pharmaceutical composition. The antibodies of the present invention may be prepared with carriers that will protect the antibody against rapid release, such as a controlled release formulation, including implants, transdermal patches, and microencapsulated delivery systems. Such carriers may include gelatin, glyceryl monostearate, glyceryl distearate, biodegradable, biocompatible polymers such as ethylene vinyl acetate, polyanhydrides, polyglycolic acid, collagen, polyorthoesters, and polylactic acid alone or with a wax, or other materials well known in the art. Methods for the preparation of such formulations are generally known to those skilled in the art. See, e.g., Sustained and Controlled Release Drug Delivery Systems, J. R. Robinson, ed., Marcel Dekker, Inc., New York, 1978.

In one embodiment, the antibodies of the present invention may be formulated to ensure proper distribution in vivo. Pharmaceutically acceptable carriers for parenteral administration include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the antibody, use thereof in the pharmaceutical compositions of the present invention is contemplated.

Pharmaceutical compositions for injection must typically be sterile and stable under the conditions of manufacture and storage. The composition may be formulated as a solution, microemulsion, liposome, or other ordered structure suitable to high drug concentration. The carrier may be a aqueous or non-aqueous solvent or dispersion medium containing for instance water, ethanol, polyols (such as glycerol, propylene glycol, polyethylene glycol, and the like), and suitable mixtures thereof, vegetable oils, such as olive oil, and injectable organic esters, such as ethyl oleate. The proper fluidity may be maintained, for example, by the use of a coating such as lecithin, by the maintenance of the required particle size in the case of dispersion and by the use of surfactants. In many cases, it will be preferable to include isotonic agents, for example, sugars, polyalcohols such as glycerol, mannitol, sorbitol, or sodium chloride in the composition. Prolonged absorption of the injectable compositions may be brought about by including in the composition an agent that delays absorption, for example, monostearate salts and gelatin. Sterile injectable solutions may be prepared by incorporating the antibody in the required amount in an appropriate solvent with one or a combination of ingredients e.g. as enumerated above, as required, followed by sterilization microfiltration. Generally, dispersions are prepared by incorporating the antibody into a sterile vehicle that contains a basic dispersion medium and the required other ingredients e.g. from those enumerated above. In the case of sterile powders for the preparation of sterile injectable solutions, examples of methods of preparation are vacuum drying and freeze-drying (lyophilization) that yield a powder of the active ingredient plus any additional desired ingredient from a previously sterile-filtered solution thereof.

Sterile injectable solutions may be prepared by incorporating the antibody in the required amount in an appropriate solvent with one or a combination of ingredients enumerated above, as required, followed by sterilization microfiltration. Generally, dispersions are prepared by incorporating the antibody into a sterile vehicle that contains a basic dispersion medium and the required other ingredients from those enumerated above. In the case of sterile powders for the preparation of sterile injectable solutions, examples of methods of preparation are vacuum drying and freeze-drying (lyophilization) that yield a powder of the active ingredient plus any additional desired ingredient from a previously sterile-filtered solution thereof.

Dosage regimens in the above methods of treatment and uses are adjusted to provide the optimum desired response (e.g., a therapeutic response). For example, a single bolus may be administered, several divided doses may be administered over time or the dose may be proportionally reduced or increased as indicated by the exigencies of the therapeutic situation. Parenteral compositions may be formulated in dosage unit form for ease of administration and uniformity of dosage. Dosage unit form as used herein refers to physically discrete units suited as unitary dosages for the subjects to be treated; each unit contains a predetermined quantity of antibody calculated to produce the desired therapeutic effect in association with the required pharmaceutical carrier. The specification for the dosage unit forms of the present invention are dictated by and directly dependent on (a) the unique characteristics of the antibody and the particular therapeutic effect to be achieved, and (b) the limitations inherent in the art of compounding such an antibody for the treatment of sensitivity in individuals.

The effective dosages and the dosage regimens for the antibodies of the invention depend on the disease or condition to be treated and may be determined by the persons skilled in the art. An exemplary, non-limiting range for a therapeutically effective amount of an antibody of the present invention is about 0.1-10 mg/kg/body weight, such as about 0.1-5 mg/kg/body weight, for example about 0.1-2 mg/kg/body weight, such as about 0.1-1 mg/kg/body weight, for instance about 0.15, about 0.2, about 0.5, about 1, about 1.5 or about 2 mg/kg/body weight.

A physician or veterinarian having ordinary skill in the art may readily determine and prescribe the effective amount of the pharmaceutical composition required. For example, the physician or veterinarian could start doses of the 8ηµ-AβpE3 antibody employed in the pharmaceutical composition at levels lower than that required in order to achieve the desired therapeutic effect and gradually increase the dosage until the desired effect is achieved. In general, a suitable daily dose of a composition of the present invention will be that amount of the antibody which is the lowest dose effective to produce a therapeutic effect. Such an effective dose will generally depend upon the factors described above. Administration may e.g. be intravenous, intramuscular, intraperitoneal, or subcutaneous, and for instance administered proximal to the site of the target. If desired, the effective daily dose of a pharmaceutical composition may be administered as two, three, four, five, six or more sub-doses administered separately at appropriate intervals throughout the day, optionally, in unit dosage forms. While it is possible for an antibody of the present invention to be administered alone, it is preferable to administer the antibody as a pharmaceutical composition as described above.

EXAMPLES

1. Humanization Approach to Generate N3pE-Aβ Specific Antibodies

The humanized and de-immunized antibodies according to the invention are humanized and de-immunized forms of monoclonal mouse antibodies that are produced by hybridoma cell line Aβ 6-1-6 (Deposit No. DSM ACC 2924), which is described in WO 2010/009987. Humanization was performed as described in WO 2017/009459. Working Example 1 disclosed on pp. 58-60 in WO 2017/009459 is hereby incorporated by reference.

2. RNA Isolation and cDNA Synthesis

As source for constant sequences, RNA of human B cells was isolated by lysis of 500 µl whole blood with 5 ml 1×FACS Lysis Solution (Becton Dickinson) for 10 minutes at room temperature. The lysate was centrifuged at 300 g for 5 min; the pellet was washed two times with PBS and was then resolved in 350 µl RA1 Buffer of Nucleo Spin® RNA II (Macherey-Nagel) and added with 3.5 µl 0.5M TCEP (SIGMA). The RNA was isolated by manufacturers' instructions. 10 µl of RNA was first incubated with 1 µl 0.5 µg/µl OligodT Primer (Invitrogen) and 1 µl 10 mM dNTPs for 5 min at 65° C. Then 4 µl of 5× First Strand Buffer (Invitrogen), 2 µl of 100 mM DTT and 0.5 µl SuperScript III Reverse Transcriptase (Invitrogen) was added to 20 µl and mix was incubated for 5 minutes at 25° C., 50 min at 50° C. and 15 min at 70° C. By PCR with primer pairs shown in Table 2, synthesized cDNA of constant region of light and heavy chain could be amplified.

TABLE 2

Primer for cloning of constant region

| SEQ ID NO | Name | Sequence |
|---|---|---|
| 43 | hkappa5' | ACTGTGGCTGCACCATCTGTCTTC |
| 44 | hkappa3' | CTAACACTCTCCCCTGTTGAAGCTC |
| 45 | hIgG1Hc5'1 | AGGGAACCCTGGTCACCGTCTCC |
| 46 | hIgG1Hc3' | TCATTTACCCGGAGACAGGGAGAGG |

For amplification of the PCR product of the light chain of clone #6 following forward and reverse primers were used:

```
                                    (SEQ ID NO: 47)
RT_chim_humKl6f:   CAAGTCAGAGCCTCTTATATAGTG;

(SEQ ID NO: 48)
RT_chim_humKl6r:   GTACCTTGCACGCAGTAATAAAC.
```

For amplification of the reference gene mouse HPRT Primer were used.

To perform the amplification 7.5 µl Sybergreen (Firma), 1 µl Primer forward (25 pmol/µl), 1 µl Primer reverse (25 pmol/µl), 5.5 µl ddH₂O and 1 µl cDNA were used in cycler.

3. Expression of Recombinant Antibody in CHO Cells by Separately Cloning LC and HC into Two Different Expression Plasmids The sequences of the light and heavy chain of the antibodies were separately cloned into two different mammalian expression vectors, pCDNA3.1 and HC-pOptiVEC respectively. To identify the optimal combination of vectors to express the recombinant antibody in CHO cell culture, different plasmid combinations were used to perform transient expressions in adherent CHO cells. In a second step, it was investigated whether different DNA ratios between LC and HC plasmid influences the expression level. With transfection of 3 µg LC-pCDNA3.1 and 1 µg HC-pOptiVEC, an increased expression level was found.

For further adherent CHO cells expression of antibody, plasmid combination of LC-pCDNA3.1 and 1 µg HC-pOptiVEC and a plasmid DNA ratio of LC 3:1 HC was used.

Freestyle™ CHO suspension cells were used in the following transfections to cultivate a higher amount of transient expressing cells which to generate recombinant antibodies. First was tested whether an excess of LC plasmid could improve the expression of antibody like in case of the adherent cells. Like in adherent CHO cells a LC to HC plasmid DNA ratio of 1:1 and 3.1 was used. Western blot analysis revealed that an excess of LC plasmid increases the expression of antibody as in the case of adherent CHO cells. By measurement of cell viability it become obvious, that the cell viability decreases to about 50% of transfected cells after 6 days. After day six, no further increase of antibody level in supernatant was detectable. Consequently, culture supernatants were harvest at day six in the case of following transfections.

To investigate if the produced antibodies are efficient transported into the cell supernatant, a cell lysate sample was applied to SDS PAGE, analyzed by Western blot. GAPDH, a housekeeping cytoplasmic protein was used for reference loading comparable amounts of cell lysate protein to the SDS gel. In cell lysate of antibody expressing CHO cells a strong band of 120 kDa occurs migrating at the same size as detected in the cell supernatant.

4. Purification of Recombinant Antibody by Protein G Chromatography

The antibody clone #6 was purified to investigate the antigen binding property of the protein in comparison with the original murine antibody. Therefore 300 ml supernatant with expressed chimeric and humanized antibody was produced and purified by Protein G chomatography. Because the amount of expressed antibody was very low, the yield was less than 0.1 µg/ml, in total 25 µg purified protein. The eluted antibody was concentrated to about 200 µg/ml and 2 µg protein was applied to SDS-PAGE following Coomassie Blue staining.

5. Stable Cell Line Generation of Humanized Antibody

The parental antibody of the humanized antibody of the present invention is the clone #6 variant disclosed in WO 2017/009459, which has the light chain variable region with the amino acid sequence:

```
                                            (SEQ ID NO: 1)
DVVMTQSPLSLPVTLGQPASISCKSSQSLLYSDGKTYLNWFQQRPGQSPR

RLTYLVSKLDSGVPDRFSGSGSGTDFTLKISRVEAEDVGVYYCVQGTHFP

FTFGGGTKVEIK,
``` which is disclosed as SEQ ID NO: 14 in WO 2017/009459; and
which has the heavy chain variable region with the amino acid sequence:

```
                                           (SEQ ID NO: 49)
QVQLVQSGAEVKKSGASVKVSCKASGYSFTGHTMNWVRQAPGQGLEWMGL

INPSNGVTRYNQKFQGRVTITRDTSTTTVHMELTSLTSEDTATYYCTREA

KREWDETYWGQGTLVTVSS;
``` which is disclosed as SEQ ID NO: 27 in WO 2017/009459.

Two clones, C06.08 and C06.09, of the parental clone #6 variant were chosen for stable cell line generation. For the generation of C06.08- and C06.09-producing Chinese hamster ovary (CHO) DG44 cells expression plasmids containing the sequences of the heavy and light chain genes for both antibodies were first generated. The plasmids were linearized, purified by isopropanol precipitation, reconstituted in 10 mM Tris pH 8.0 and used in transfections as follows: $1\times10^6$ CHO-DG44 cells were suspended in 100 µL Nucleofector solution V (Lonza) and mixed with 10 µg linearized vector DNA. The suspension was pulsed with an electroporator Amaxa Nucleofector II (Lonza). Subsequently, 500 µL CD CHO medium (Invitrogen) was added and the transfected cell pools were cultivated for 24 hours.

For the generation of stable mini pools (MPs) transfected cell pools were combined one day after transfection, transferred either into CD CHO medium and seeded at 2000 cells/well and 4000 cells/well in 96-well plates, respectively, or transferred into CD CHO medium with 2.5 nM Methotrexate (MTX) and seeded at 4000 cells/well in 96-well plates. After a cultivation period of 21 (C06.08) or 27 (C06.09) days, 20 MPs were transferred to 24-well plates. On day 22 or day 28 post transfection, the MPs were transferred to 12-well plates and the MPs were expanded to 6-well plates on day 34 or day 48. On day 34 (C06.08) or 48 (C06.09), pools were transferred into selective medium with 30 nM MTX to induce the amplification process and antibody expression titers were determined by Octet measurements.

Results

TABLE 2

Analysis of C06.08 stable Mini Pools

| Day 1 | Day 21 Selected MPs | Day 34 to 72 MTX amplification |
|---|---|---|
| 2000 cells/well | #1-10 | No cell growth; very low or no antibody production |
| 4000 cells/well | #11-15 | |
| 4000 cells/well & 2.5 nM MTX | #15-20 | |

TABLE 3

Analysis of C06.09 stable Mini Pools

| Day 1 | Day 27 Selected MPs | Day 48 to 52 MTX amplification |
|---|---|---|
| 2000 cells/well | #1-10 | No cell growth; very low or no antibody production |
| 4000 cells/well | #11-15 | |
| 4000 cells/well & 2.5 nM MTX | #15-20 | |

As summarized in Tables 2 and 3, all MPs displayed poor cells growth, very low to no detectable antibody production (<10 µg/cell/day) and many MPs did not survive the MTX amplification. Repeat transfection experiments with a new set of reagents lead to similar results, while transfection with control vectors resulted in normal protein expression levels. These results suggested that genome-integrated 006.08 and 006.09 proteins may have inherent toxic effects on CHO-DG44 cells, e.g. these proteins may trigger cell death due to the overexpression of misfolded 006.08 and 006.09 proteins in the nucleus. Further modifications to the primary sequence of C06.08 and C06.09 are warranted, which correct protein misfolding and eliminate the induction of CHO-DG44 cell death.

PBD-C06 Modifications to Improve Protein Folding and Expression

Figure 2:
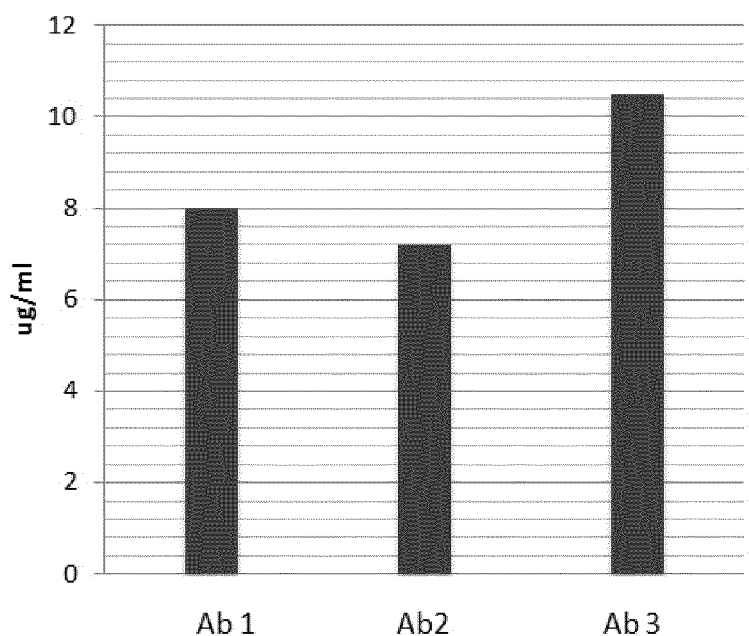
FIG. 2 shows the influence of the point mutations in the heavy chain on transient expression (A) and target binding (B) of individual variants of the antibody of the invention. All antibodies tested contain the variable part of the light chain of SEQ ID NO. 1 and the K324A mutation in the heavy chain.
- Ab 1: contains the two mutations K12V and S14P in the variable part of the heavy chain compared to the parental sequence SEQ ID NO: 49;
- Ab 2: contains the mutation N55D in the variable part of the heavy chain compared to the parental sequence SEQ ID NO: 49;
- Ab 3: contains the three mutations K12V, S14P and N55D in the variable part of the heavy chain compared to the parental sequence SEQ ID NO: 49
Figure 2:
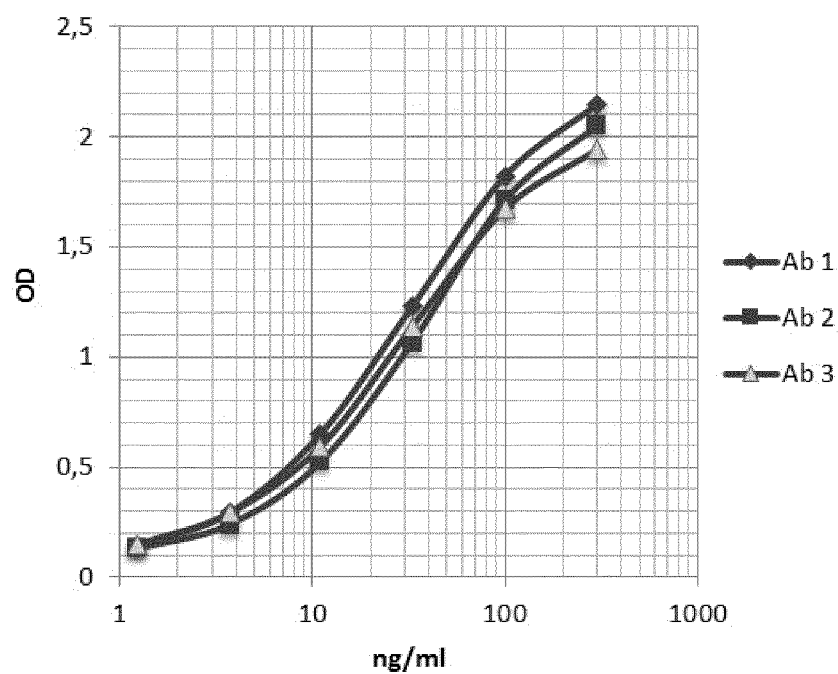

In silico analysis of the C06 amino acid sequences revealed several stretches of amino acids (spots) in the framework regions of the heavy chain that were proposed to negatively influence protein folding. To examine whether these spots could be exchanged with alternative amino acids that improve protein expression, four individual heavy chain mutations (K12V, S14P, N55D and F64V) were first synthesized and tested individually in transient transfections for protein expression together with the light chain of SEQ ID NO: 17. Target binding studies revealed that the F64V modification prevented antibody binding. In a second set of experiments, combinations of each mutation were integrated in pairs and triplets into individual heavy chain genes and tested in combination with the light chain of SEQ ID NO: 17 for expression and target binding studies (FIGS. 1 and 2).

Results

The combination of the K12V, S14P and N55D mutations resulted in the best transient C06 expression titers and optimal target binding properties (FIGS. 1 and 2) and a respective clone comprising all these three mutations was chosen for CHO-DG44 stable transfection studies.

Stable Expression of the Humanized Antibody in CHO-DG44 Cells

The parental CHO-DG44 cells were originally obtained from Gibco, Life Technologies (Freedom™ DG44 Kit) now managed by Thermo Fisher Scientific. The CHO cells line is DHFR-deficient and cGMP banked with documentation.

Transfection of CHO-DG44 cells with vectors expressing humanized antibody comprising the light chain of SEQ ID NO: 1 and heavy chain of SEQ ID NO: 2 (which comprises the K12V, S14P and N55D mutations) resulted in severalfold improved number of CHO-DG44 clones compared to prior transfection attempts (see above). Furthermore, after MTX exposure multiple clones with high target antibody expression titers were identified, revealing that the K12V, S14P and N55D mutations improved antibody folding and expression after stable integration into the CHO-DG44 genome. Prolonged stable expression was confirmed under fed-batch conditions over extended periods of cultivation confirming that the chosen alterations (K12V, S14P and N55D) in the heavy chain of parental clone #6 facilitated proper folding and expression in CHO-DG44 cells.

Figure 3:
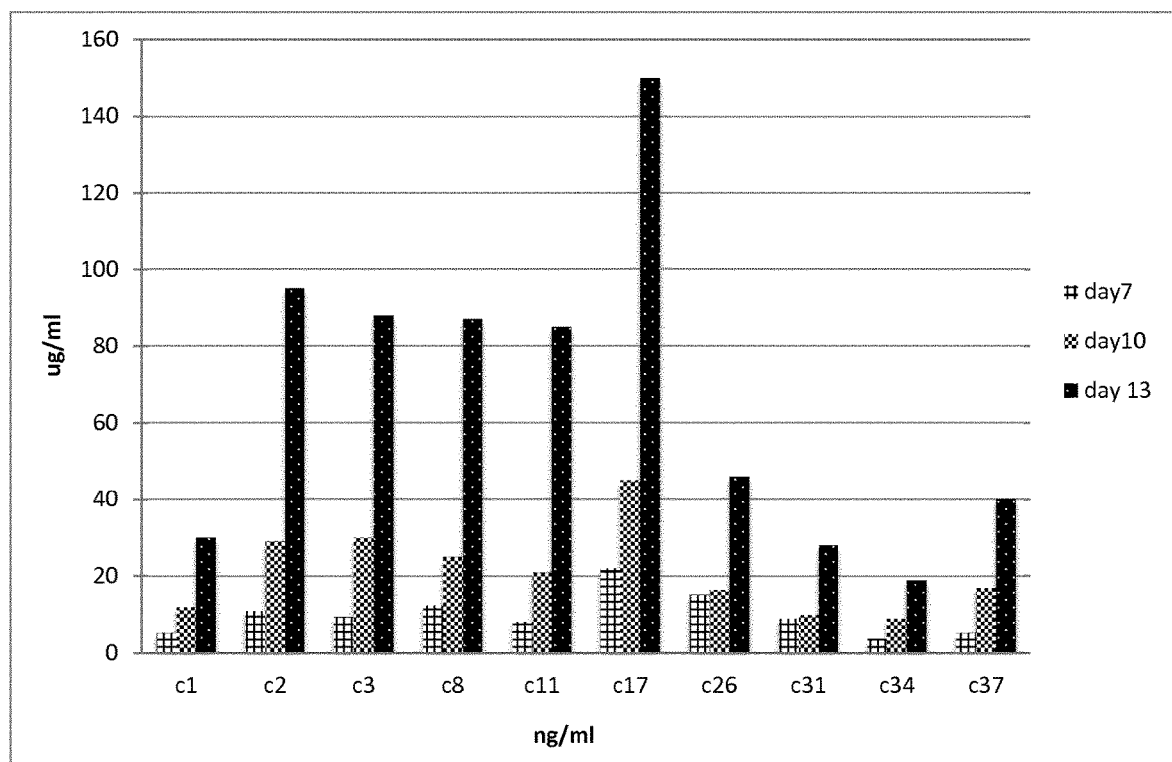
FIG. 3 shows CHO-DG44 clones expressing the antibody with the variable part of the light chain of SEQ ID NO: 1 and the variable part of the heavy chain of SEQ ID NO: 2, seven, ten and 13 days after seeding wells of a 24-well plate from colonies picked from a 96-well plate.
Figure 4:
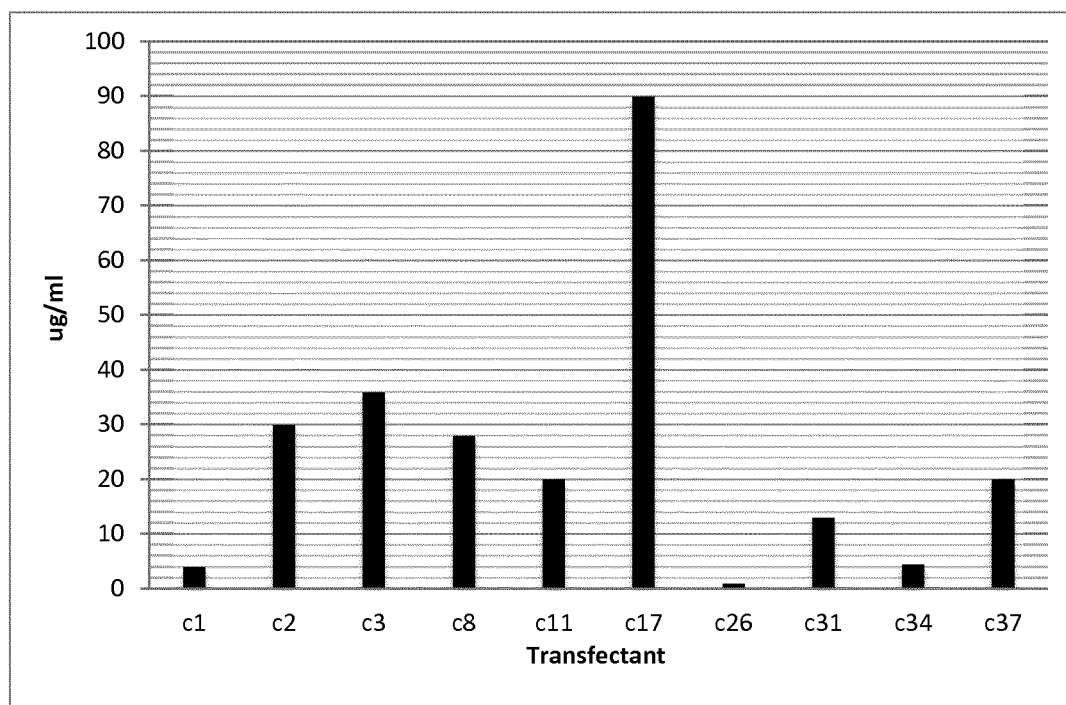
FIG. 4 shows CHO-DG44 expression titers after gene amplification through MTX exposure (Day 7).

Additional stable cell lines were obtained after further vector and electroporation optimization. Initial transfectants, prior to gene amplification, expressed high levels of antibody early after isolation and expansion to 0.5 ml cultures in a 24-well plate (FIG. 3). Production titers at day 7 further increased after the first MTX exposure (FIG. 4), suggesting that these clones, in particular c17, will be a much more efficient producer.

Summary

Four heavy chain mutations were tested individually to see if they would increase antibody expression in transiently transfected HEK293 cells. Three of these mutations significantly increased antibody expression while the fourth decreased expression. Combinations of the individual mutations were also tried in pairs and the triple mutation, all of which were expressed well and purified by protein A chromatography. Upon Biacore analysis it was found that the combination of four mutations decreased binding while the combination of specific mutations K12V, S14P and N55D were expressed well and had optimal binding properties. No changes in the light chain sequences were necessary for high expression.

Studies were performed in stably transfected CHO DG44 cells and higher levels of antibody expression were obtained after initial selection and following gene amplification induced by step-wise increases of methotrexate (MTX). It was further observed that higher levels of antibody expression did not prevent good cell growth. In summary, the transfection campaign lead to the identification of several new candidates for CMC manufacturing.

5. Surface Plasmon Resonance Measurement to Analyze the Binding of the Humanized and De-Immunized Antibody to Monomeric Aβ Peptides Surface Plasmon Resonance measurement was used to investigate the binding efficacy of the antibody, which comprises the variable part of the light chain with SEQ ID NO. 1 and the the variable part of the heavy chain with SEQ ID NO. 2. To prevent mass transfer and avidity effects during measurement, the following procedure was used.

First a polyclonal α-human antibody was coupled to an SPR-Chip subsequent loaded with the antibody until the Response Unit was more than 1000.

Kinetic measurements were performed at different concentrations (of 5 to 1000 nM) of Aβ-peptide. The graphs of the measured series are shown as an overlay plot with the sensorgrams, corrected by the sensogram measuring the running buffer, aligned at the time of injection and the baseline adjusted to zero before injection. The results are evaluated according to a simple 1:1 interaction model (Langmuir fit), which promote the $k_{off}$ and $k_{on}$ rate constants.

Apparent kinetic constants according to the 1:1 Langmuir fitting are listed in Table 4. Due to the fact that the antibody is non-covalently bound to the chip surface, small amounts of antibody molecules were washed out during the measurement. Therefore the Rmax values were fitted locally for every single sensogramm.

TABLE 4

Statistics of Langmuir fit in kinetics of humanized and de-immunized antibody clone#6

| Aβ peptide | $K_D$ | $k_a$, $(s^{-1}M^{-1})$ | $k_d$, $(s^{-1})$ | $R_{max}$ | RI | Chi$^2$ |
|---|---|---|---|---|---|---|
| Aβ (pE3-18) | 8.22 nM | 4.79 × 10$^5$ | 3.94 × 10$^{-3}$ | Global (43.9 RU) | local | 0.462 |
| Aβ (3-18) | 1.21 μM | 3.09 × 10$^3$ | 3.74 × 10$^{-3}$ | Global (40.8 RU) | local | 0.243 |
| Aβ (1-18) | 23.1 μM | 173 | 3.99 × 10$^{-3}$ | Global (57.4 RU) | local | 0.400 |
| Aβ (4-18) | 28.3 μM | — | — | 48.9 RU | — | 0.0815 |

Binding to Aβ (pE3-18) The qualitative and visual inspection of the recorded sensorgrams shows a good shape for the association as well as the dissociation phase. Furthermore, a concentration dependent elevation of the response signal and an increase of the initial slope in the association phase were observed. The maximal SPR signals were ~44 RU, which was within the optimal range measuring binding kinetics without or negligible mass transport effects. No baseline drift was observed, therefore the data were evaluated using the Langmuir 1:1 binding model obtaining the binding properties of this interaction and quality of the fit (Tab. 4).

Binding to Aβ (3-18)

The qualitative and visual inspection of the recorded sensorgrams shows a good shape for the association as well as the dissociation phase. Furthermore, a concentration dependent elevation of the response signal and an increase of the initial slope in the association phase were observed. The maximal SPR signals were ~44 RU, which was within the optimal range measuring binding kinetics without or negligible mass transport effects. No baseline drift was observed, therefore the data were evaluated using the Langmuir 1:1 binding model obtaining the binding properties of this interaction and quality of the fit (Tab. 4).

Binding to Aβ (1-18)

The qualitative and visual inspection of the recorded sensorgrams shows a typical shape for a weak binding appropriate to the used peptide concentrations. A slight baseline drift was observed; therefore, the data were fitted using the Langmuir 1:1 binding with drifting baseline model. Evaluation of the kinetic data (Tab. 4) yielded a dissociation constant of 23.1 µM, which was above the highest measured Aβ(1-18) concentration. Furthermore, the calculated Rmax value was significantly higher than the response values of the highest concentration. Both facts indicate that the obtained binding properties be definitely in the range KD>10 µM.

Binding to Aβ (4-18)

The qualitative and visual inspection of the recorded sensorgrams shows a typical shape for a very weak binding appropriate to the used peptide concentrations. Because of a very fast association and dissociation the data cannot be evaluated kinetically, therefore a steady-state model was used. The evaluation of the response signals in steady-state (Tab. 4) yielded a dissociation constant of 28.3 µM, which was above the highest measured Aβ (4-18) concentration. Furthermore, the calculated Rmax value was significantly higher than the response values of the highest concentration. Both facts indicate that the obtained binding properties must be definitely in the range $K_D$>10 µM.

6. Binding to Aβ fibrils and Aβ oligomers

Fibrils of Aβ (1-42) peptides were generated according standard protocols at pH 8.7 and 37° C. After complete fibrillation the structures were aspirated in 60 µl, diluted in 140 µl running buffer and loaded onto a sensor chip by use of capture antibodies with a flow rate of 1 µl/min. Then, the system was washed until getting a stable baseline. About 100 RU of the Aβ (1-42) fibrils were captured onto the sensor chip.

Oligomers of Aβ (1-42) peptides were generated according to the ACUMEN protocol in Ham's F12 medium overnight at 4° C. and separated from aggregated Aβ by centrifugation. Afterwards the oligomers were aspirated in 20 µl, diluted in 60 µl running buffer and loaded onto a sensor chip by use of capture antibodies with a flow rate of 1 µl/min. Then, the system was washed overnight with 100 µl/min getting a stable baseline. About 300 RU of the of Aβ (1-42) oligomers were captured onto the sensor chip.

For fibrils of Aβ (1-42) peptides: After getting a stable baseline the interaction analysis was performed by 11 consecutive injections (10 µM, 30 µM, 90 µM, 270 µM, 810 µM, 2.43 nM, 7.29 nM, 21.87 nM, 65.61 nM, 196.83 nM and 590.49 nM) of the parental antibody clone #6 as disclosed in WO 2017/009459 and the humanized and de-immunized antibody clone #6 of the present invention with 30 µl/min, 480 sec contact time and 1200 sec dissociation time. The obtained sensorgrams were evaluated using five consecutive concentrations (starting with the first injection showing binding) and the Single Cycle Kinetics model with a global fit of Rmax and baseline drift and local fits of the bulk effect of every injection.

For oligomers of Aβ (1-42) peptides: After getting a stable baseline the interaction analysis was performed by 11 consecutive injections (10 pM, 30 pM, 90 pM, 270 pM, 810 pM, 2.43 nM, 7.29 nM, 21.87 nM, 65.61 nM, 196.83 nM and 590.49 nM) the parental antibody clone #6 as disclosed in WO 2017/009459 and the humanized and de-immunized antibody clone #6 of the present invention with 30 µl/min, 480 sec contact time and 3600 sec dissociation time. The obtained sensorgrams were evaluated using five consecutive concentrations (starting with the first injection showing binding) and the Single Cycle Kinetics model with a global fit of Rmax and baseline drift and local fits of the bulk effect of every injection.

Results

TABLE 5

Binding to fibrils Aβ(1-42) peptides

| Antibody | $K_D$ | ka $M^{-1}s^{-1}$ | kd $10^{-5} s^{-1}$ | Rmax | Chi$^2$ |
|---|---|---|---|---|---|
| A | 65.9 pM | 9.9 · 10$^5$ | 6.53· | 26 RU | 0.336 |
| B | 1.67 nM | 5.97 · 10$^4$ | 9.99· | 19.2 RU | 0.602 |

TABLE 6

Binding to oligomers of Aβ(1-42) peptides

| Antibody | $K_D$ | ka $M^{-1}s^{-1}$ | kd $10^{-4} s^{-1}$ | Rmax | Chi2 |
|---|---|---|---|---|---|
| A | 7.61 nM | 1.86 · 10$^4$ | 1.42· | 442 RU | 6.31 |
| B | 269 nM | 868 | 2.33· | 216 RU | 0.284 |

In tables 5 and 6,

A is the parental antibody clone #6 disclosed in WO 2017/009459 with a variable region of the light chain of SEQ ID NO: 1 and a variable region of the heavy chain of SEQ ID NO: 49; and B is the humanized and de-immunized antibody clone #6 of the present invention with a variable region of the light chain of SEQ ID NO: 1 and a variable region of the heavy chain of SEQ ID NO: 2.

As can be seen from these results, the invention provides antibodies and fragments thereof, wherein the antibodies show an increased selectivity towards oligomers and/or fibrils of Aβ peptides. The antibodies of the present invention show a manifold, such as 10 times, 25 times, 50 times, 100 times, 150 times, 200 times, 250 times or more than 250 times lower binding constant ($K_D$ value) for binding to oligomers and/or fibrils of Aβ (1-42) than comparable monoclonal antibodies known in the prior art, in particular compared to the parental antibody disclosed in WO 2017/009459. Accordingly, the antibodies of the present invention, which were established to selectively bind to Aβ N3pE peptides, are more specific for Aβ N3pE peptides and show a decreased cross-reactivity against Aβ peptides other than Aβ N3pE.

7. Binding to Fc Gamma Receptors

The binding of two antibodies, which either comprised the heavy chain of SEQ ID NO: 19 or the K324A mutant variant thereof (SEQ ID NO: 18), to different Fc gamma receptors (CD16A, CD32A, CD32B, and CD64) was compared.

The K324A mutant was produced by site-directed mutagenesis. The binding was measured in a FACS based bioassay to Chinese Hamster Ovary (CHO) cells stably expressing full length human CD16A, CD32A, CD32B, or CD64. Both antibodies were incubated with each cell line at 7 different concentrations for one hour followed by washing. Receptor-bound H6 or H67 was detected with fluorochrome conjugated-anti-Fab'. Binding capacity was measured by FACS and the Kd and Bmax were calculated by non-linear regression.

Results: Both antibodies showed comparable binding to all receptors.

8. Binding to C1q

The binding of two antibodies, which either comprised the heavy chain of SEQ ID NO: 19 or the K324A mutant variant thereof (SEQ ID NO: 18), to C1q was compared in order to better characterize the effector functions of the antibodies.

A number of assay formats of binding of the antibodies to C1q was tested, including a) direct binding of the two antibodies to the plate and then biding to C1q in solution; and b) streptavidin coated plates first incubated with biotinylated pE-Aβ peptide, binding to antibodies and then C1q.

In summary, format a) produced best results. The procedure is summarized below:

The ELISA plate was coated with the antibody, comprising the heavy chain of SEQ ID NO: 19, the K324A mutant variant thereof (SEQ ID NO: 18), and a K324A control that does not bind C1q at 10, 8, 6, 4, 3, 2, 1 and 0 µg/ml in triplicate and incubated at 4° C. overnight. Next day, the plate was washed three times with 1×PBS and then blocked with 1% BSA in 1×PBS at 50 µl/well. C1q (Sigma, Cat. #C1740) was added to each well at 2 µg/ml in blocking buffer and incubated for 1 hour at room temperature. The plate was then washed three times with 200 µl of 1×PBS. Anti-C1q-HRP (Thermo, Cat. #PA1-84324) was added to the plate to detect the binding at a 1:250 dilution in blocking buffer (50 µl/well) for 1 hour. The plate was washed again three times with 200 µl of 1×PBS. 50 µl of TMB (Invitrogen, Cat. #002023) was added to each well to visualize the interaction (Invitrogen, Cat. #002023) for 2 min. 50 µl of stop solution ((1M Sulfuric Acid) was added to each well before reading the absorbance at 450 nm.

Results: The antibody, which comprised the wild-type heavy chain of SEQ ID NO: 19 did bind to C1q. The K324A mutant variant thereof (comprising the heavy chain of SEQ ID NO: 18), did not bind to C1q.

9. Immunohistochemistry

With IHC the antigen Aβ N3pE can be localized in cerebral tissue sections. Therefore the antibodies of the invention were used for detection of Aβ N3pE.

For the IHC human cerebral tissue sections of the hippocampus and the frontal cortex from AD patients and furthermore cerebral tissue sections of hippocampus from existing animal models for Alzheimer's disease as described herein can be used. These mouse models show increased brain Aβ levels followed by development of neuritic plaques. The tissue sections were paraffin-embedded and serial cut. The sections were stained with hematoxylin to colored nuclei of cells and then immunostained with the anti Aβ N3pE antibodies of the invention. The tissue section preparation and staining were performed in accordance with standard methodology.

10. Treatment of Alzheimer Mice In Vivo

A total of 62 male mice were utilized in this study. Prior to the start of immunization, four mice of an existing mouse model for Alzheimer's disease (avg. 5.6 mo±0.45) mice were sacrificed as baseline controls to assess cerebral Aβ plaque burden at the commencement of treatment. The remaining mice were divided into four groups and received the following treatment: 250 µl sterile PBS (n=12; avg. 5.89 mo±0.13), 200 µg of an antibody of the invention. A group of age- and gender-matched Wt littermates were injected with 250 µl PBS (n=12; avg. 5.80 mo±0.12) and served as behavioral controls. Mice were treated with a total volume of 250 µl (antibody or PBS) via intraperitoneal injection for 28 weeks.

Euthanasia and Tissue Preparation

Mice were euthanized, perfused and plasma harvested at 6 months (baseline) or 13 months of age. The brain was extracted and divided sagittally. The hippocampus, cortex and cerebellum were dissected from one hemisphere and snap frozen for biochemical analyses. The other hemisphere was drop-fixed in 4% parafomaldehyde (Electron Microscopy Sciences) for 24 h at 4° C., cryoprotected in graded sucrose solutions at 4° C. and embedded in OCT compound (Tissue Tek).

The invention claimed is:

1. An antibody wherein said antibody comprises CDR regions:

```
                                                    (SEQ ID NO: 3)
    VLCDR1: SSQSLLYSDGKTYLN;

(SEQ ID NO: 4)
    VLCDR2: LVSKLDS;
    and (SEQ ID NO: 5)
    VLCDR3: VQGTHFP
``` in the light chain and CDR regions:

```
                                                    (SEQ ID NO: 6)
    VHCDR1: GYSFTGHTMN;

(SEQ ID NO: 7)
    VHCDR2: LINPSDGVTRYNQKFQG;
    and (SEQ ID NO: 8)
    VHCDR3: EAKREWDETY
``` in the heavy chain
wherein the antibody specifically binds a pyroglutamate carrying N-terminus of the Aβ N3pE epitope.

2. The antibody of claim 1, wherein the variable part of the light chain of said antibody comprises the amino acid sequence:

```
                                                    (SEQ ID NO: 1)
DVVMTQSPLSLPVTLGQPASISCKSSQSLLYSDGKTYLNWFQQRPGQSPR

RLTYLVSKLDSGVPDRFSGSGSGTDFTLKISRVEAEDVGVYYCVQGTHFP

FTFGGGTKVEIK.
```

3. The antibody of claim 1, wherein the variable part of the heavy chain of said antibody comprises the amino acid sequence:

```
                                                    (SEQ ID NO: 2)
QVQLVQSGAEVVKPGASVKVSCKASGYSFTGHTMNWVRQAPGQGLEWMGL

INPSDGVTRYNQKFQGRVTITRDTSTTTVHMELTSLTSEDTATYYCTREA

KREWDETYWGQGTLVTVSS.
```

4. The antibody of claim 1 wherein the light chain comprises the amino acid sequence:

```
                                                    (SEQ ID NO: 17)
DVVMTQSPLSLPVTLGQPASISCKSSQSLLYSDGKTYLNWFQQRPGQSPR

RLTYLVSKLDSGVPDRFSGSGSGTDFTLKISRVEAEDVGVYYCVQGTHFP

FTFGGGTKVEIKRTVAAPSVFIFPPSDEQLKSGTASVVCLLNNFYPREAK

VQWKVDNALQSGNSQESVTEQDSKDSTYSLSSTLTLSKADYEKHKVYACE

VTHQGLSSPVTKSFNRGEC.
```

5. The antibody of claim 1 wherein the heavy chain comprises the amino acid sequence:

(SEQ ID NO: 18)
QVQLVQSGAEVVKPGASVKVSCKASGYSFTGHTMNWVRQAPGQGLEWMGL

INPSDGVTRYNQKFQGRVTITRDTSTTTVHMELTSLTSEDTATYYCTREA

KREWDETYWGQGTLVTVSSASTKGPSVFPLAPSSKSTSGGTAALGCLVKD

YFPEPVTVSWNSGALTSGVHTFPAVLQSSGLYSLSSVVTVPSSSLGTQTY

ICNVNHKPSNTKVDKKVEPKSCDKTHTCPPCPAPELLGGPSVFLFPPKPK

DTLMISRTPEVTCVVVDVSHEDPEVKFNWYVDGVEVHNAKTKPREEQYNS

TYRVVSVLTVLHQDWLNGKEYKCAVSNKALPAPIEKTISKAKGQPREPQV

YTLPPSRDELTKNQVSLTCLVKGFYPSDIAVEWESNGQPENNYKTTPPVL

DSDGSFFLYSKLTVDKSRWQQGNVFSCSVMHEALHNHYTQKSLSLSPGK.

6. The antibody of claim 1 wherein the heavy chain comprises the amino acid sequence:

(SEQ ID NO: 19)
QVQLVQSGAEVVKPGASVKVSCKASGYSFTGHTMNWVRQAPGQGLEWMGL

INPSDGVTRYNQKFQGRVTITRDTSTTTVHMELTSLTSEDTATYYCTREA

KREWDETYWGQGTLVTVSSASTKGPSVFPLAPSSKSTSGGTAALGCLVKD

YFPEPVTVSWNSGALTSGVHTFPAVLQSSGLYSLSSVVTVPSSSLGTQTY

ICNVNHKPSNTKVDKKVEPKSCDKTHTCPPCPAPELLGGPSVFLFPPKPK

DTLMISRTPEVTCVVVDVSHEDPEVKFNWYVDGVEVHNAKTKPREEQYNS

TYRVVSVLTVLHQDWLNGKEYKCKVSNKALPAPIEKTISKAKGQPREPQV

YTLPPSRDELTKNQVSLTCLVKGFYPSDIAVEWESNGQPENNYKTTPPVL

DSDGSFFLYSKLTVDKSRWQQGNVFSCSVMHEALHNHYTQKSLSLSPGK.

7. The antibody according to claim 1 wherein the antibody binds specifically to an epitope selected from the group consisting of

| | |
|---|---|
| pEFRHDSGYEVHHQKLV, | (SEQ ID NO: 23) |
| pEFRHDSGYEVHHQKL, | (SEQ ID NO: 24) |
| pEFRHDSGYEVHHQK, | (SEQ ID NO: 25) |
| pEFRHDSGYEVHHQ, | (SEQ ID NO: 26) |
| pEFRHDSGYEVHH, | (SEQ ID NO: 27) |
| pEFRHDSGYEVH, | (SEQ ID NO: 28) |
| pEFRHDSGYEV, | (SEQ ID NO: 29) |
| pEFRHDSGYE, | (SEQ ID NO: 30) |
| pEFRHDSGY, | (SEQ ID NO: 31) |
| pEFRHDSG, | (SEQ ID NO: 32) |
| pEFRHDS, | (SEQ ID NO: 33) |
| pEFRHD | (SEQ ID NO: 34) |
| pEFRH, and | (SEQ ID NO: 35) |
| pEFR. | (SEQ ID NO: 36) |

8. The antibody according to claim 1 wherein the antibody binds to an Aβ N3pE variant, wherein the Aβ N3pE variant is defined as pE-Aβ$_{3-x}$, and wherein x is defined as an integer between 19 and 42.

9. The antibody of claim 8, wherein the Aβ N3pE variant is selected from:
pE-Aβ$_{3-38}$,
pE-Aβ$_{3-40}$,
pE-Aβ$_{3-42}$.

10. The antibody according to claim 1 wherein said antibody does not bind to epitopes that do not carry a pyroglutamate at the N-terminus.

11. A pharmaceutical composition comprising the antibody according to claim 1.

12. The pharmaceutical composition of claim 11, further comprising a further biologically active substance and/or a pharmaceutically acceptable carrier and/or a diluent and/or an excipient.

13. The pharmaceutical composition of claim 12, wherein said further biologically active substance is selected from the group consisting of neutron-transmission enhancers, psychotherapeutic drugs, acetylcholine esterase inhibitors, calcium-channel blockers, biogenic amines, benzodiazepine tranquillizers, acetylcholine synthesis enhancers, acetylcholine storage enhancers, acetylcholine release enhancers, acetylcholine postsynaptic receptor agonists, monoamine oxidase-A inhibitors, monoamine oxidase-B inhibitors, N-methyl-D-aspartate glutamate receptor antagonists, non-steroidal anti-inflammatory drugs, antioxidants, and serotonergic receptor antagonists.

14. The pharmaceutical composition of claim 12, wherein said further biologically active substance is selected from the group consisting of compounds effective against oxidative stress, anti-apoptotic compounds, metal chelators, inhibitors of DNA repair, 3-amino-1-propanesulfonic acid (3 APS), 1,3-propanedisulfonate (1,3PDS), α-secretase activators, β-secretase inhibitors, γ-secretase inhibitors, tau proteins, neurotransmitter, β-sheet breakers, attractants for amyloid beta clearing/depleting cellular components, inhibitors of N-terminal truncated amyloid beta, anti-inflammatory molecules, cholinesterase inhibitors (ChEIs), MI agonists, amyloid modifying drugs, tau modifying drugs, nutritive supplements, cholinesterase inhibitors (ChEIs), memantine, and glutaminyl cyclase inhibitors.

* * * * *

SEQUENCE LISTING

```
<160> NUMBER OF SEQ ID NOS: 49

<210> SEQ ID NO 1
<211> LENGTH: 112
<212> TYPE: PRT
<213> ORGANISM: Artificial sequence
<220> FEATURE:
<223> OTHER INFORMATION: Recombinant Polypeptide

<400> SEQUENCE: 1

Asp Val Val Met Thr Gln Ser Pro Leu Ser Leu Pro Val Thr Leu Gly
1               5                   10                  15

Gln Pro Ala Ser Ile Ser Cys Lys Ser Ser Gln Ser Leu Leu Tyr Ser
            20                  25                  30

Asp Gly Lys Thr Tyr Leu Asn Trp Phe Gln Gln Arg Pro Gly Gln Ser
        35                  40                  45

Pro Arg Arg Leu Thr Tyr Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Val Gln Gly
                85                  90                  95
```

```
Thr His Phe Pro Phe Thr Phe Gly Gly Gly Thr Lys Val Glu Ile Lys
            100                 105                 110
```

<210> SEQ ID NO 2
<211> LENGTH: 119
<212> TYPE: PRT
<213> ORGANISM: Artificial sequence
<220> FEATURE:
<223> OTHER INFORMATION: Recombinant Polypeptide

<400> SEQUENCE: 2

```
Gln Val Gln Leu Val Gln Ser Gly Ala Glu Val Val Lys Pro Gly Ala
1               5                   10                  15

Ser Val Lys Val Ser Cys Lys Ala Ser Gly Tyr Ser Phe Thr Gly His
            20                  25                  30

Thr Met Asn Trp Val Arg Gln Ala Pro Gly Gln Gly Leu Glu Trp Met
        35                  40                  45

Gly Leu Ile Asn Pro Ser Asp Gly Val Thr Arg Tyr Asn Gln Lys Phe
    50                  55                  60

Gln Gly Arg Val Thr Ile Thr Arg Asp Thr Ser Thr Thr Val His
65                  70                  75                  80

Met Glu Leu Thr Ser Leu Thr Ser Glu Asp Thr Ala Thr Tyr Tyr Cys
                85                  90                  95

Thr Arg Glu Ala Lys Arg Glu Trp Asp Glu Thr Tyr Trp Gly Gln Gly
            100                 105                 110

Thr Leu Val Thr Val Ser Ser
        115
```

<210> SEQ ID NO 3
<211> LENGTH: 15
<212> TYPE: PRT
<213> ORGANISM: Artificial sequence
<220> FEATURE:
<223> OTHER INFORMATION: Recombinant peptide

<400> SEQUENCE: 3

```
Ser Ser Gln Ser Leu Leu Tyr Ser Asp Gly Lys Thr Tyr Leu Asn
1               5                   10                  15
```

<210> SEQ ID NO 4
<211> LENGTH: 7
<212> TYPE: PRT
<213> ORGANISM: Artificial sequence
<220> FEATURE:
<223> OTHER INFORMATION: Synthetic peptide

<400> SEQUENCE: 4

```
Leu Val Ser Lys Leu Asp Ser
1               5
```

<210> SEQ ID NO 5
<211> LENGTH: 7
<212> TYPE: PRT
<213> ORGANISM: Artificial sequence
<220> FEATURE:
<223> OTHER INFORMATION: Recombinant peptide

<400> SEQUENCE: 5

```
Val Gln Gly Thr His Phe Pro
1               5
```

<210> SEQ ID NO 6

```
<211> LENGTH: 10
<212> TYPE: PRT
<213> ORGANISM: Artificial sequence
<220> FEATURE:
<223> OTHER INFORMATION: Recombinant peptide

<400> SEQUENCE: 6

Gly Tyr Ser Phe Thr Gly His Thr Met Asn
1               5                   10

<210> SEQ ID NO 7
<211> LENGTH: 17
<212> TYPE: PRT
<213> ORGANISM: Artificial sequence
<220> FEATURE:
<223> OTHER INFORMATION: Recombinant peptide

<400> SEQUENCE: 7

Leu Ile Asn Pro Ser Asp Gly Val Thr Arg Tyr Asn Gln Lys Phe Gln
1               5                   10                  15

Gly

<210> SEQ ID NO 8
<211> LENGTH: 10
<212> TYPE: PRT
<213> ORGANISM: Artificial sequence
<220> FEATURE:
<223> OTHER INFORMATION: Recombinant peptide

<400> SEQUENCE: 8

Glu Ala Lys Arg Glu Trp Asp Glu Thr Tyr
1               5                   10

<210> SEQ ID NO 9
<211> LENGTH: 336
<212> TYPE: DNA
<213> ORGANISM: Artificial sequence
<220> FEATURE:
<223> OTHER INFORMATION: Recombinant nucleic acid

<400> SEQUENCE: 9
gacgtggtga tgactcagtc tccactctcc ctgcccgtca cccttggaca gccggcctcc      60
atctcctgca gtcaagtca gagcctcctg cactccgacg gcaagaccta cttgaactgg     120
ttccagcaga ggccaggcca gtctccaagg cgcctgacct atctggtgtc taagctggac     180
tctggggtcc cagacagatt cagcggcagt gggtcaggca ctgacttcac actgaagatc     240
agcagggtgg aggctgagga tgtcggagtc tactactgcg tgcaaggtac acacttccca     300
ttcacgttcg gcggagggac caaggtggaa atcaaa                              336

<210> SEQ ID NO 10
<211> LENGTH: 357
<212> TYPE: DNA
<213> ORGANISM: Artificial sequence
<220> FEATURE:
<223> OTHER INFORMATION: Synthetic nucleic acid

<400> SEQUENCE: 10
caggtgcagc tcgtgcagtc tggggctgag gtggtgaagc aggtgcctc agtgaaggtc        60 tcctgcaagg catctggtta ctcattcact ggtcacacca tgaactgggt gcgacaggcc     120
cctggacaag gcttgagtg gatgggactc atcaatcctt ccgatggtgt tactaggtac     180
aaccagaagt tccagggcag agtcaccatc accagggaca cgtccacgac caccgttcac    240
```

```
atggagctga ccagcctgac atctgaggac acggccacct actactgtac gagagaggcg    300
aaacgggagt gggacgagac ttactggggc cagggaaccc tggtcaccgt ctcctca       357
```

<210> SEQ ID NO 11
<211> LENGTH: 45
<212> TYPE: DNA
<213> ORGANISM: Artificial sequence
<220> FEATURE:
<223> OTHER INFORMATION: Recombinant nucleic acid

<400> SEQUENCE: 11

```
tcaagtcaga gcctcctgca ctccgacggc aagacctact tgaac                    45
```

<210> SEQ ID NO 12
<211> LENGTH: 21
<212> TYPE: DNA
<213> ORGANISM: Artificial sequence
<220> FEATURE:
<223> OTHER INFORMATION: Recombinant nucleic acid

<400> SEQUENCE: 12

```
ctggtgtcta agctggactc t                                              21
```

<210> SEQ ID NO 13
<211> LENGTH: 21
<212> TYPE: DNA
<213> ORGANISM: Artificial sequence
<220> FEATURE:
<223> OTHER INFORMATION: Recombinant nucleic acid

<400> SEQUENCE: 13

```
gtgcaaggta cacacttccc a                                              21
```

<210> SEQ ID NO 14
<211> LENGTH: 30
<212> TYPE: DNA
<213> ORGANISM: Artificial sequence
<220> FEATURE:
<223> OTHER INFORMATION: Recombinant nucleic acid

<400> SEQUENCE: 14

```
ggttactcat tcactggtca caccatgaac                                     30
```

<210> SEQ ID NO 15
<211> LENGTH: 51
<212> TYPE: DNA
<213> ORGANISM: Artificial sequence
<220> FEATURE:
<223> OTHER INFORMATION: Recombinant nucleic acid

<400> SEQUENCE: 15

```
ctcatcaatc cttccgatgg tgttactagg tacaaccaga agttccaggg c              51
```

<210> SEQ ID NO 16
<211> LENGTH: 30
<212> TYPE: DNA
<213> ORGANISM: Artificial sequence
<220> FEATURE:
<223> OTHER INFORMATION: Recombinant nucleic acid

<400> SEQUENCE: 16

```
gaggcgaaac gggagtggga cgagacttac                                     30
```

<210> SEQ ID NO 17
<211> LENGTH: 219

```
<212> TYPE: PRT
<213> ORGANISM: Artificial sequence
<220> FEATURE:
<223> OTHER INFORMATION: Recombinant polypeptide

<400> SEQUENCE: 17

Asp Val Val Met Thr Gln Ser Pro Leu Ser Leu Pro Val Thr Leu Gly
1               5                   10                  15

Gln Pro Ala Ser Ile Ser Cys Lys Ser Ser Gln Ser Leu Leu Tyr Ser
            20                  25                  30

Asp Gly Lys Thr Tyr Leu Asn Trp Phe Gln Gln Arg Pro Gly Gln Ser
        35                  40                  45

Pro Arg Arg Leu Thr Tyr Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Val Gln Gly
                85                  90                  95

Thr His Phe Pro Phe Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 18
<211> LENGTH: 449
<212> TYPE: PRT
<213> ORGANISM: Artificial sequence
<220> FEATURE:
<223> OTHER INFORMATION: Recombinant polypeptide

<400> SEQUENCE: 18

Gln Val Gln Leu Val Gln Ser Gly Ala Glu Val Val Lys Pro Gly Ala
1               5                   10                  15

Ser Val Lys Val Ser Cys Lys Ala Ser Gly Tyr Ser Phe Thr Gly His
            20                  25                  30

Thr Met Asn Trp Val Arg Gln Ala Pro Gly Gln Gly Leu Glu Trp Met
        35                  40                  45

Gly Leu Ile Asn Pro Ser Asp Gly Val Thr Arg Tyr Asn Gln Lys Phe
    50                  55                  60

Gln Gly Arg Val Thr Ile Thr Arg Asp Thr Ser Thr Thr Thr Val His
65                  70                  75                  80

Met Glu Leu Thr Ser Leu Thr Ser Glu Asp Thr Ala Thr Tyr Tyr Cys
                85                  90                  95

Thr Arg Glu Ala Lys Arg Glu Trp Asp Glu Thr Tyr Trp Gly Gln Gly
            100                 105                 110
```

```
Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
        130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Ala Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 19
<211> LENGTH: 449
<212> TYPE: PRT
<213> ORGANISM: Artificial sequence
<220> FEATURE:
<223> OTHER INFORMATION: Recombinant polypeptide

<400> SEQUENCE: 19

Gln Val Gln Leu Val Gln Ser Gly Ala Glu Val Val Lys Pro Gly Ala
1               5                   10                  15
```

-continued

```
Ser Val Lys Val Ser Cys Lys Ala Ser Gly Tyr Ser Phe Thr Gly His
            20                  25                  30
Thr Met Asn Trp Val Arg Gln Ala Pro Gly Gln Gly Leu Glu Trp Met
        35                  40                  45
Gly Leu Ile Asn Pro Ser Asp Gly Val Thr Arg Tyr Asn Gln Lys Phe
    50                  55                  60
Gln Gly Arg Val Thr Ile Thr Arg Asp Thr Ser Thr Thr Thr Val His
65                  70                  75                  80
Met Glu Leu Thr Ser Leu Thr Ser Glu Asp Thr Ala Thr Tyr Tyr Cys
                85                  90                  95
Thr Arg Glu Ala Lys Arg Glu Trp Asp Glu Thr Tyr Trp Gly Gln Gly
            100                 105                 110
Thr Leu Val Thr Val Ser Ser Ala Ser Thr Lys Gly Pro Ser Val Phe
        115                 120                 125
Pro Leu Ala Pro Ser Ser Lys Ser Thr Ser Gly Gly Thr Ala Ala Leu
    130                 135                 140
Gly Cys Leu Val Lys Asp Tyr Phe Pro Glu Pro Val Thr Val Ser Trp
145                 150                 155                 160
Asn Ser Gly Ala Leu Thr Ser Gly Val His Thr Phe Pro Ala Val Leu
                165                 170                 175
Gln Ser Ser Gly Leu Tyr Ser Leu Ser Ser Val Val Thr Val Pro Ser
            180                 185                 190
Ser Ser Leu Gly Thr Gln Thr Tyr Ile Cys Asn Val Asn His Lys Pro
        195                 200                 205
Ser Asn Thr Lys Val Asp Lys Lys Val Glu Pro Lys Ser Cys Asp Lys
    210                 215                 220
Thr His Thr Cys Pro Pro Cys Pro Ala Pro Glu Leu Leu Gly Gly Pro
225                 230                 235                 240
Ser Val Phe Leu Phe Pro Pro Lys Pro Lys Asp Thr Leu Met Ile Ser
                245                 250                 255
Arg Thr Pro Glu Val Thr Cys Val Val Val Asp Val Ser His Glu Asp
            260                 265                 270
Pro Glu Val Lys Phe Asn Trp Tyr Val Asp Gly Val Glu Val His Asn
        275                 280                 285
Ala Lys Thr Lys Pro Arg Glu Glu Gln Tyr Asn Ser Thr Tyr Arg Val
    290                 295                 300
Val Ser Val Leu Thr Val Leu His Gln Asp Trp Leu Asn Gly Lys Glu
305                 310                 315                 320
Tyr Lys Cys Lys Val Ser Asn Lys Ala Leu Pro Ala Pro Ile Glu Lys
                325                 330                 335
Thr Ile Ser Lys Ala Lys Gly Gln Pro Arg Glu Pro Gln Val Tyr Thr
            340                 345                 350
Leu Pro Pro Ser Arg Asp Glu Leu Thr Lys Asn Gln Val Ser Leu Thr
        355                 360                 365
Cys Leu Val Lys Gly Phe Tyr Pro Ser Asp Ile Ala Val Glu Trp Glu
    370                 375                 380
Ser Asn Gly Gln Pro Glu Asn Asn Tyr Lys Thr Thr Pro Pro Val Leu
385                 390                 395                 400
Asp Ser Asp Gly Ser Phe Phe Leu Tyr Ser Lys Leu Thr Val Asp Lys
                405                 410                 415
Ser Arg Trp Gln Gln Gly Asn Val Phe Ser Cys Ser Val Met His Glu
            420                 425                 430
Ala Leu His Asn His Tyr Thr Gln Lys Ser Leu Ser Leu Ser Pro Gly
```

Lys

<210> SEQ ID NO 20
<211> LENGTH: 657
<212> TYPE: DNA
<213> ORGANISM: Artificial sequence
<220> FEATURE:
<223> OTHER INFORMATION: Recombinant nucleic acid

<400> SEQUENCE: 20

```
gacgtggtga tgactcagtc tccactctcc ctgcccgtca cccttggaca gccggcctcc      60
atctcctgca agtcaagtca gagcctcctg cactccgacg gcaagaccta cttgaactgg     120
ttccagcaga ggccaggcca gtctccaagg cgcctgacct atctggtgtc taagctggac     180
tctggggtcc cagacagatt cagcggcagt gggtcaggca ctgacttcac actgaagatc     240
agcagggtgg aggctgagga tgtcggagtc tactactgcg tgcaaggtac acacttccca     300
ttcacgttcg gcggagggac caaggtggaa atcaaaagga ccgtggccgc accctctgtg     360
ttcatcttcc cccccagcga cgagcagctg aagagcggca ctgcatctgt cgtgtgtctg     420
ctgaacaact tctacccaag ggaggcgaaa gtgcagtgga aggtagacaa cgccttgcaa     480
tccggcaact cccaggagag cgtgaccgag caggacagca agactcaac ctacagcctg     540
agcagtactt tgaccctgtc taaggccgat tacgagaagc acaaggtgta cgcctgcgag     600
gtaaccccacc agggactgag ctctcccgtg accaagagct caacagggg cgagtgc       657
```

<210> SEQ ID NO 21
<211> LENGTH: 1347
<212> TYPE: DNA
<213> ORGANISM: Artificial sequence
<220> FEATURE:
<223> OTHER INFORMATION: Recombinant nucleic acid

<400> SEQUENCE: 21

```
caggtgcagc tcgtgcagtc tggggctgag gtggtgaagc aggtgcctc agtgaaggtc       60
tcctgcaagg catctggtta ctcattcact ggtcacacca tgaactgggt gcgacaggcc     120
cctggacaag ggcttgagtg gatgggactc atcaatcctt ccgatggtgt tactaggtac     180
aaccagaagt tccagggcag agtcaccatc accagggaca cgtccacgac caccgttcac     240
atggagctga ccagcctgac atctgaggac acggccacct actactgtac gagagaggcg     300
aaacgggagt gggacgagac ttactggggc cagggaaccc tggtcaccgt ctcctcagcc     360
agcactaagg gcccgagcgt gttccccctc gcccctagca gtaagagcac cagcggtggc     420
acggcggcac ttggctgctt ggttaaggac tacttcccag agccgtgac cgtgtcctgg     480
aactctgggg cacttaccag tggcgtgcac accttccccg ctgtactgca gagcagcggc     540
ttgtacagct tgtcttccgt cgtaacggtg cccagcagca gcttgggaac ccagacctac     600
atctgcaacg taaaccacaa gccatccaac accaaggtag acaaaaaggt cgaacccaag     660
tcctgcgaca gacccacac ctgtccaccc tgtcctgcac ccgagctcct gggaggtccc     720
agcgttttcc tgttccctcc aaagccaaag gatacctga tgatcagcag gaccccgag      780
gtgacctgcg tggtggtgga cgtgagccac gaagaccctg aggtcaagtt caactggtac     840
gttgatgggg tggaggtaca caatgccaag accaaacctc gagaggagca atacaacagc     900
acctaccgag ttgtgagcgt gcttaccgtg ctgcaccagg actggctgaa cggcaaggag     960
tacaagtgcg ctgtgagcaa caaggctctg ccggctccca tcgagaaaag catcagcaag    1020
```

```
gccaagggcc agcccaggga gccacaggtt tacacgttgc cccccctcaag ggacgagttg    1080 accaagaacc aggtttccct cacgtgcctt gtgaagggct tctacccag cgacatcgcc     1140 gtggaatggg agagcaacgg gcagcccgag aacaactaca agacgacccc ccctgttctg    1200
gacagcgacg gctctttctt cctgtattca aagctcaccg tggacaaaag caggtggcag    1260
cagggtaatg tgttctcctg cagcgtgatg catgaggccc tgcataacca ctacacccaa    1320
aagagcttga gcctctcccc cggtaag                                         1347

<210> SEQ ID NO 22
<211> LENGTH: 1347
<212> TYPE: DNA
<213> ORGANISM: Artificial sequence
<220> FEATURE:
<223> OTHER INFORMATION: Recombinant nucleic acid

<400> SEQUENCE: 22
caggtgcagc tcgtgcagtc tggggctgag gtggtgaagc caggtgcctc agtgaaggtc     60
tcctgcaagg catctggtta ctcattcact ggtcacacca tgaactgggt gcgacaggcc    120
cctggacaag ggcttgagtg gatgggactc atcaatcctt ccgatggtgt tactaggtac    180
aaccagaagt tccagggcag agtcaccatc accagggaca cgtccacgac caccgttcac    240
atggagctga ccagcctgac atctgaggac acggccacct actactgtac gagagaggcg    300 aaacggggagt gggacgagac ttactggggc cagggaaccc tggtcaccgt ctcctcagcc    360
agcactaagg gcccgagcgt gttccccctc gcccctagca gtaagagcac cagcggtggc    420
acggcggcac ttggctgctt ggttaaggac tacttcccag agcccgtgac cgtgtcctgg    480
aactctgggg cacttaccag tggcgtgcac accttcccg ctgtactgca gagcagcggc    540
ttgtacagct tgtcttccgt cgtaacggtg cccagcagca gcttgggaac ccagacctac    600
atctgcaacg taaaccacaa gccatccaac accaaggtag acaaaaaggt cgaacccaag    660
tcctgcgaca agacccacac ctgtccaccc tgtcctgcac ccgagctcct gggaggtccc    720
agcgttttcc tgttccctcc aaagccaaag gataccctga tgatcagcag gaccccccgag    780 gtgacctgcg tggtggtgga cgtgagccac gaagaccctg aggtcaagtt caactggtac    840
gttgatgggg tggaggtaca caatgccaag accaaacctc gagaggagca atacaacagc    900
acctaccgag ttgtgagcgt gcttaccgtg ctgcaccagg actggctgaa cggcaaggag    960
tacaagtgca aggtgagcaa caaggctctg ccggctccca tcgagaagac catcagcaag    1020
gccaagggcc agcccaggga gccacaggtt tacacgttgc cccccctcaag ggacgagttg    1080 accaagaacc aggtttccct cacgtgcctt gtgaagggct tctacccag cgacatcgcc     1140 gtggaatggg agagcaacgg gcagcccgag aacaactaca agacgacccc ccctgttctg    1200
gacagcgacg gctctttctt cctgtattca aagctcaccg tggacaaaag caggtggcag    1260
cagggtaatg tgttctcctg cagcgtgatg catgaggccc tgcataacca ctacacccaa    1320
aagagcttga gcctctcccc cggtaag                                         1347

<210> SEQ ID NO 23
<211> LENGTH: 16
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
```

<223> OTHER INFORMATION: PYRROLIDONE CARBOXYLIC ACID

<400> SEQUENCE: 23

Glu Phe Arg His Asp Ser Gly Tyr Glu Val His His Gln Lys Leu Val
1               5                   10                  15

<210> SEQ ID NO 24
<211> LENGTH: 15
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: PYRROLIDONE CARBOXYLIC ACID

<400> SEQUENCE: 24

Glu Phe Arg His Asp Ser Gly Tyr Glu Val His His Gln Lys Leu
1               5                   10                  15

<210> SEQ ID NO 25
<211> LENGTH: 14
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: PYRROLIDONE CARBOXYLIC ACID

<400> SEQUENCE: 25

Glu Phe Arg His Asp Ser Gly Tyr Glu Val His His Gln Lys
1               5                   10

<210> SEQ ID NO 26
<211> LENGTH: 13
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: PYRROLIDONE CARBOXYLIC ACID

<400> SEQUENCE: 26

Glu Phe Arg His Asp Ser Gly Tyr Glu Val His His Gln
1               5                   10

<210> SEQ ID NO 27
<211> LENGTH: 12
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: PYRROLIDONE CARBOXYLIC ACID

<400> SEQUENCE: 27

Glu Phe Arg His Asp Ser Gly Tyr Glu Val His His
1               5                   10

<210> SEQ ID NO 28
<211> LENGTH: 11
<212> TYPE: PRT

```
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: PYRROLIDONE CARBOXYLIC ACID

<400> SEQUENCE: 28

Glu Phe Arg His Asp Ser Gly Tyr Glu Val His
1               5                   10

<210> SEQ ID NO 29
<211> LENGTH: 10
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: PYRROLIDONE CARBOXYLIC ACID

<400> SEQUENCE: 29

Glu Phe Arg His Asp Ser Gly Tyr Glu Val
1               5                   10

<210> SEQ ID NO 30
<211> LENGTH: 9
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: PYRROLIDONE CARBOXYLIC ACID

<400> SEQUENCE: 30

Glu Phe Arg His Asp Ser Gly Tyr Glu
1               5

<210> SEQ ID NO 31
<211> LENGTH: 8
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: PYRROLIDONE CARBOXYLIC ACID

<400> SEQUENCE: 31

Glu Phe Arg His Asp Ser Gly Tyr
1               5

<210> SEQ ID NO 32
<211> LENGTH: 7
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: PYRROLIDONE CARBOXYLIC ACID

<400> SEQUENCE: 32

Glu Phe Arg His Asp Ser Gly
```

-continued

```
<210> SEQ ID NO 33
<211> LENGTH: 6
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: PYRROLIDONE CARBOXYLIC ACID

<400> SEQUENCE: 33

Glu Phe Arg His Asp Ser
1               5

<210> SEQ ID NO 34
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: PYRROLIDONE CARBOXYLIC ACID

<400> SEQUENCE: 34

Glu Phe Arg His Asp
1               5

<210> SEQ ID NO 35
<211> LENGTH: 4
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: PYRROLIDONE CARBOXYLIC ACID

<400> SEQUENCE: 35

Glu Phe Arg His
1

<210> SEQ ID NO 36
<211> LENGTH: 3
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: PYRROLIDONE CARBOXYLIC ACID

<400> SEQUENCE: 36

Glu Phe Arg
1

<210> SEQ ID NO 37
<211> LENGTH: 42
<212> TYPE: PRT
<213> ORGANISM: Human

<400> SEQUENCE: 37

Asp Ala Glu Phe Arg His Asp Ser Gly Tyr Glu Val His His Gln Lys
```

-continued

```
                1               5                   10                  15
Leu Val Phe Phe Ala Glu Asp Val Gly Ser Asn Lys Gly Ala Ile Ile
                    20                  25                  30

Gly Leu Met Val Gly Gly Val Val Ile Ala
            35                  40
```

<210> SEQ ID NO 38
<211> LENGTH: 40
<212> TYPE: PRT
<213> ORGANISM: Human

<400> SEQUENCE: 38

```
Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
                    20                  25                  30

Gly Leu Met Val Gly Gly Val Val
            35                  40
```

<210> SEQ ID NO 39
<211> LENGTH: 38
<212> TYPE: PRT
<213> ORGANISM: Human

<400> SEQUENCE: 39

```
Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
                    20                  25                  30

Gly Leu Met Val Gly Gly
            35
```

<210> SEQ ID NO 40
<211> LENGTH: 40
<212> TYPE: PRT
<213> ORGANISM: Human

<400> SEQUENCE: 40

```
Glu Phe Arg His Asp Ser Gly Tyr Glu Val His His Gln Lys Leu Val
1               5                   10                  15

Phe Phe Ala Glu Asp Val Gly Ser Asn Lys Gly Ala Ile Ile Gly Leu
                    20                  25                  30

Met Val Gly Gly Val Val Ile Ala
            35                  40
```

<210> SEQ ID NO 41
<211> LENGTH: 38
<212> TYPE: PRT
<213> ORGANISM: Human

<400> SEQUENCE: 41

```
Glu Phe Arg His Asp Ser Gly Tyr Glu Val His His Gln Lys Leu Val
1               5                   10                  15

Phe Phe Ala Glu Asp Val Gly Ser Asn Lys Gly Ala Ile Ile Gly Leu
                    20                  25                  30

Met Val Gly Gly Val Val
            35
```

<210> SEQ ID NO 42
<211> LENGTH: 36

```
<212> TYPE: PRT
<213> ORGANISM: Human

<400> SEQUENCE: 42

Glu Phe Arg His Asp Ser Gly Tyr Glu Val His His Gln Lys Leu Val
1               5                   10                  15

Phe Phe Ala Glu Asp Val Gly Ser Asn Lys Gly Ala Ile Ile Gly Leu
            20                  25                  30

Met Val Gly Gly
        35

<210> SEQ ID NO 43
<211> LENGTH: 24
<212> TYPE: DNA
<213> ORGANISM: Artificial sequence
<220> FEATURE:
<223> OTHER INFORMATION: PCR primer

<400> SEQUENCE: 43
actgtggctg caccatctgt cttc                                          24

<210> SEQ ID NO 44
<211> LENGTH: 25
<212> TYPE: DNA
<213> ORGANISM: Artificial sequence
<220> FEATURE:
<223> OTHER INFORMATION: PCR primer

<400> SEQUENCE: 44
ctaacactct ccctgttga agctc                                          25

<210> SEQ ID NO 45
<211> LENGTH: 23
<212> TYPE: DNA
<213> ORGANISM: Artificial sequence
<220> FEATURE:
<223> OTHER INFORMATION: PCR primer

<400> SEQUENCE: 45
agggaaccct ggtcaccgtc tcc                                           23

<210> SEQ ID NO 46
<211> LENGTH: 25
<212> TYPE: DNA
<213> ORGANISM: Artificial sequence
<220> FEATURE:
<223> OTHER INFORMATION: PCR primer

<400> SEQUENCE: 46
tcatttaccc ggagacaggg agagg                                         25

<210> SEQ ID NO 47
<211> LENGTH: 24
<212> TYPE: DNA
<213> ORGANISM: Artificial sequence
<220> FEATURE:
<223> OTHER INFORMATION: PCR primer

<400> SEQUENCE: 47
caagtcagag cctcttatat agtg                                          24

<210> SEQ ID NO 48
<211> LENGTH: 23
<212> TYPE: DNA
<213> ORGANISM: Artificial sequence
```

```
<220> FEATURE:
<223> OTHER INFORMATION: PCR primer

<400> SEQUENCE: 48
gtaccttgca cgcagtaata aac                                            23

<210> SEQ ID NO 49
<211> LENGTH: 119
<212> TYPE: PRT
<213> ORGANISM: Artificial sequence
<220> FEATURE:
<223> OTHER INFORMATION: Recombinant polypeptide

<400> SEQUENCE: 49

Gln Val Gln Leu Val Gln Ser Gly Ala Glu Val Lys Lys Ser Gly Ala
1               5                   10                  15

Ser Val Lys Val Ser Cys Lys Ala Ser Gly Tyr Ser Phe Thr Gly His
            20                  25                  30

Thr Met Asn Trp Val Arg Gln Ala Pro Gly Gln Gly Leu Glu Trp Met
        35                  40                  45

Gly Leu Ile Asn Pro Ser Asn Gly Val Thr Arg Tyr Asn Gln Lys Phe
    50                  55                  60

Gln Gly Arg Val Thr Ile Thr Arg Asp Thr Ser Thr Thr Val His
65                  70                  75                  80

Met Glu Leu Thr Ser Leu Thr Ser Glu Asp Thr Ala Thr Tyr Tyr Cys
                85                  90                  95

Thr Arg Glu Ala Lys Arg Glu Trp Asp Glu Tyr Trp Gly Gln Gly
            100                 105                 110

Thr Leu Val Thr Val Ser Ser
        115
```